(12) United States Patent
Sung et al.

(10) Patent No.: US 7,439,328 B2
(45) Date of Patent: Oct. 21, 2008

(54) TCTEX-1-RELATED POLYPEPTIDES

(75) Inventors: Ching-Hwa Sung, New York, NY (US); Jen-Zen Chuang, New York, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/428,122

(22) Filed: Jun. 30, 2006

(65) Prior Publication Data

US 2007/0117747 A1  May 24, 2007

Related U.S. Application Data

(60) Provisional application No. 60/696,205, filed on Jul. 1, 2005.

(51) Int. Cl.
*C07K 14/00* (2006.01)
*C12P 21/04* (2006.01)

(52) U.S. Cl. ................. 530/350; 530/402; 435/69.7

(58) Field of Classification Search .................. None
See application file for complete search history.

(56) References Cited

OTHER PUBLICATIONS

Wells, Biochemistry 29:8509-8517, 1990.*
Ngo et al.,The Protein Folding Problem and Tertiary Structure Prediction, pp. 492-495, 1994.*
Chuang et al. Dev Cell 9: 75-86, 2005.*
Bork, Genome Research 10:398-400, 2000.*
Skolnick et al., Trends in Biotech. 18(1): 34-39, 2000.*
Doerks et al., Trends in Genetics 14:248-250, 1998.*
Smith et al., Nature Biotechnology 15:1222-1223, 1997.*
Brenner, Trends in Genetics 15:132-133, 1999.*
Bork et al., Trends in Genetics 12:425-427, 1996.*
Kai et al. "Molecular cloning of Fyn-associated molecules in the mouse central nervous system." *Journal Neuroscience Research*, vol. 48, pp. 407-424, 1997.

Chuang, Jen-Zen, et al.; "A 29 kDa Intracellular Chloride Channel p64H1 Is Associated with Large Dense-Core Vesicles in Rat Hippocampal Neurons"; *The Journal of Neuroscience*, Apr. 15, 1999, 19(8): pp. 2919-2928.
Chuang, Jen-Zen; "Dynein light chain Tctex-1, a novel marker for adult hippocampal progenitors, is essential for neuronal development"; *Mol. Biol. Cell*, 2003; 14 (Suppl.): p. 1753.
Chuang, Jen-Zen, et al.; "Subunit Heterogeneity of Cytoplasmic Dynein: Differential Expression of 14 kDa Dynein Light Chains in Rat Hippocampus"; *The Journal of Neuroscience*, Aug. 1, 2001, 21 (15); pp. 5501-5512.
Tai, Andrew W., et al.; "Cytoplasmic Dynein Regulation by Subunit Heterogeneity and Its Role in Apical Transport," *The Journal of Cell Biology*, vol. 153, No. 7, Jun. 25, 2001, pp. 1499-1509.
Tai, Andrew W., et al.; "Localization of Tctex-1, a Cytoplasmic Dynein Light Chain, to the Golgi Apparatus and Evidence for Dynein Complex Heterogeneity"; *The Journal of Biological Chemistry*; vol. 273, No. 31 Issue of Jul. 31, 1998, pp. 19639-19649.
Tai, Andrew W., et al.; "Rhodopsin's Carboxy-Terminal Cytoplasmic Tail Acts as a Membrane Receptor for Cytoplasmic Dynein by Binding to the Dynein Light Chain Tctex-1"; *Cell*, vol. 97; Jun. 25, 1999; pp. 877-887.
Yano, Hiroko, et al.; "Association of Trk Neurotrophin Receptors with Components of the Cytoplasmic Dynein Motor", *The Journal of Neuroscience*, 2001, vol. 21 RC 125, pp. 1-7.

* cited by examiner

*Primary Examiner*—Jeffrey Stucker
*Assistant Examiner*—Aditi Dutt
(74) *Attorney, Agent, or Firm*—Scott E. Kamholz; Foley Hoag LLP

(57) ABSTRACT

A polypeptide may include an amino acid sequence having at least about 95% identity to the amino acid sequence of SEQ ID NO: 42, wherein a residue at position 94 of the polypeptide is an amino acid other than threonine or wherein a residue at position 82 of the polypeptide is an amino acid other than serine. A polypeptide may include at least the first 14 residues and at most the first 92 residues of an amino acid sequence starting with residue 1 of, and having at least about 95% identity to, the amino acid sequence of SEQ ID NO: 1, 3, 5, 7, 9, 11, 13, 15, 16, or 17. Such polypeptide may stimulate neurite outgrowth or neurogenesis. A nucleic acid may encode the polypeptide. A vector may include the nucleic acid. A host cell, such as an embryonic stem cell, may include the vector.

12 Claims, 14 Drawing Sheets

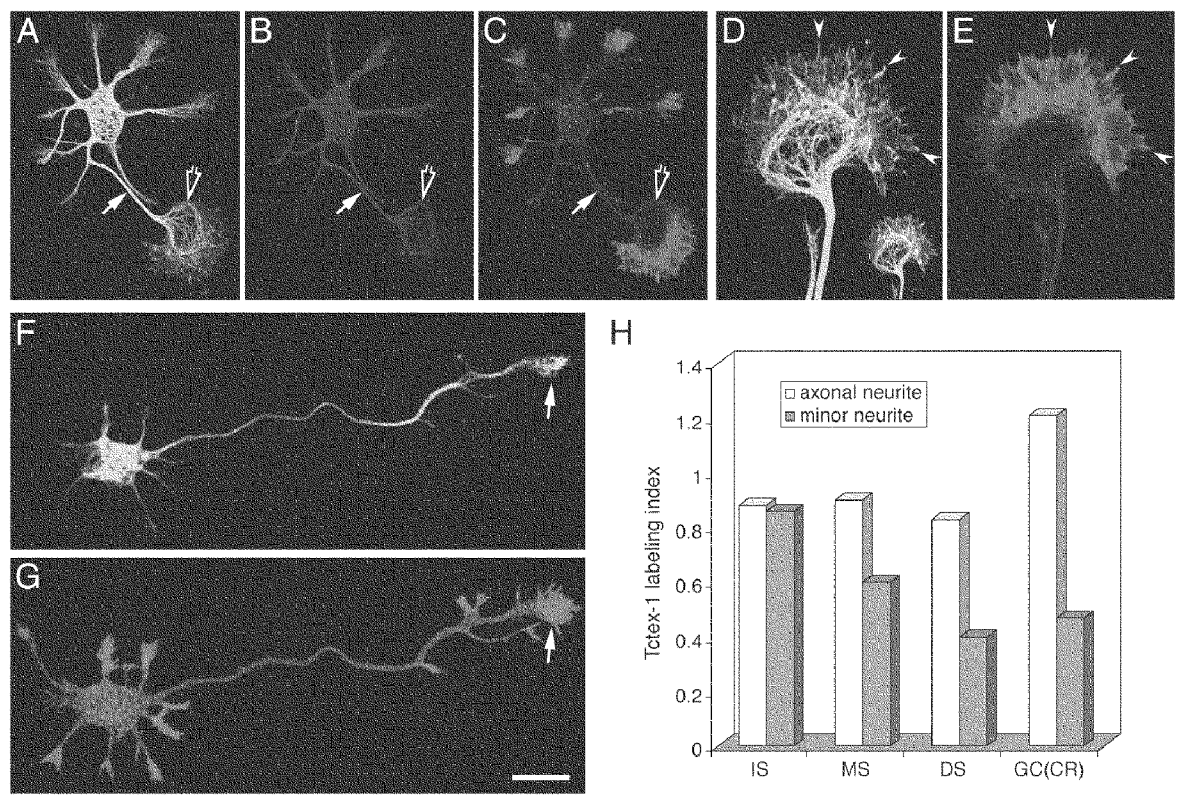
Figures 1A-H

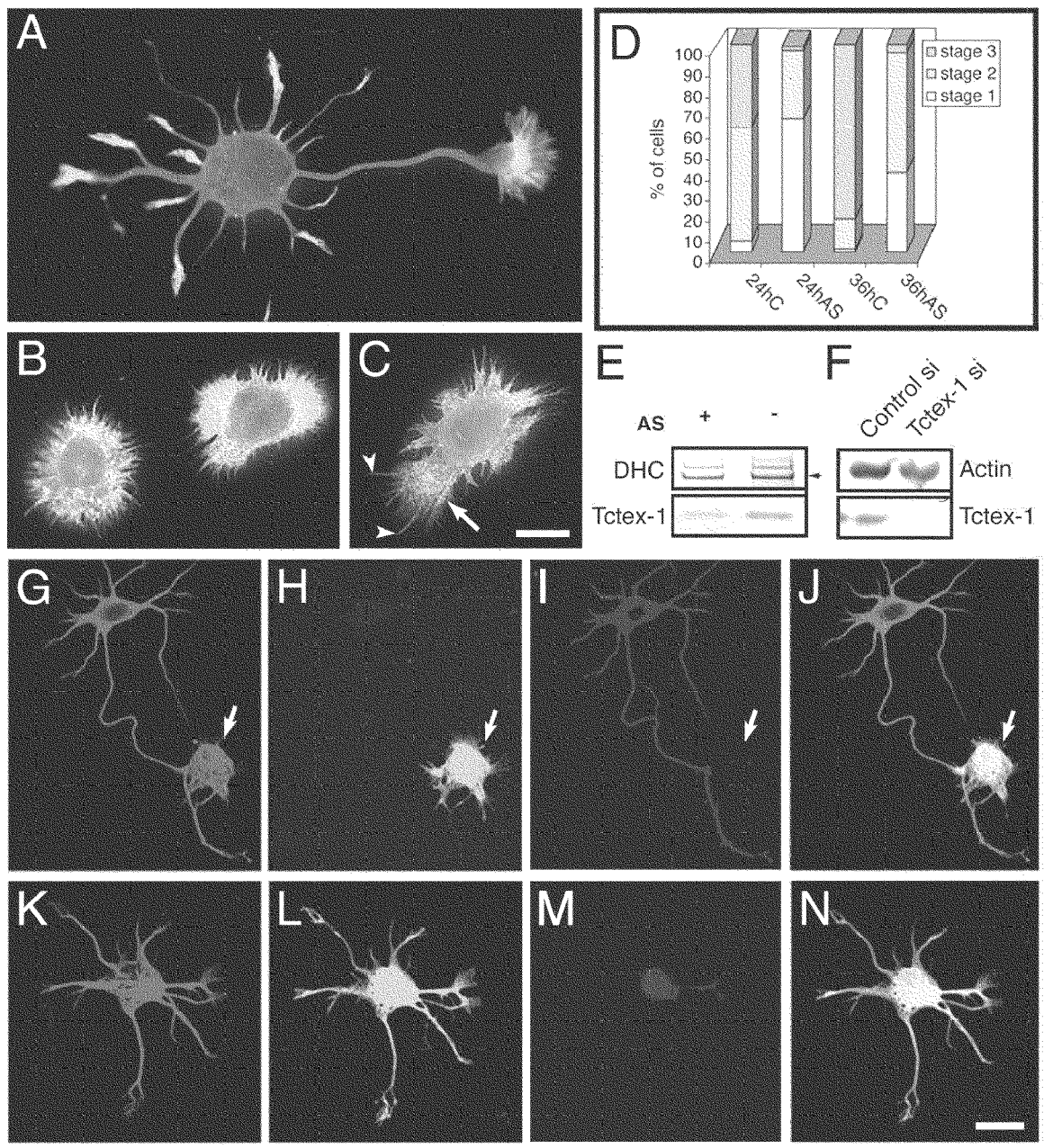
Figures 2A-N

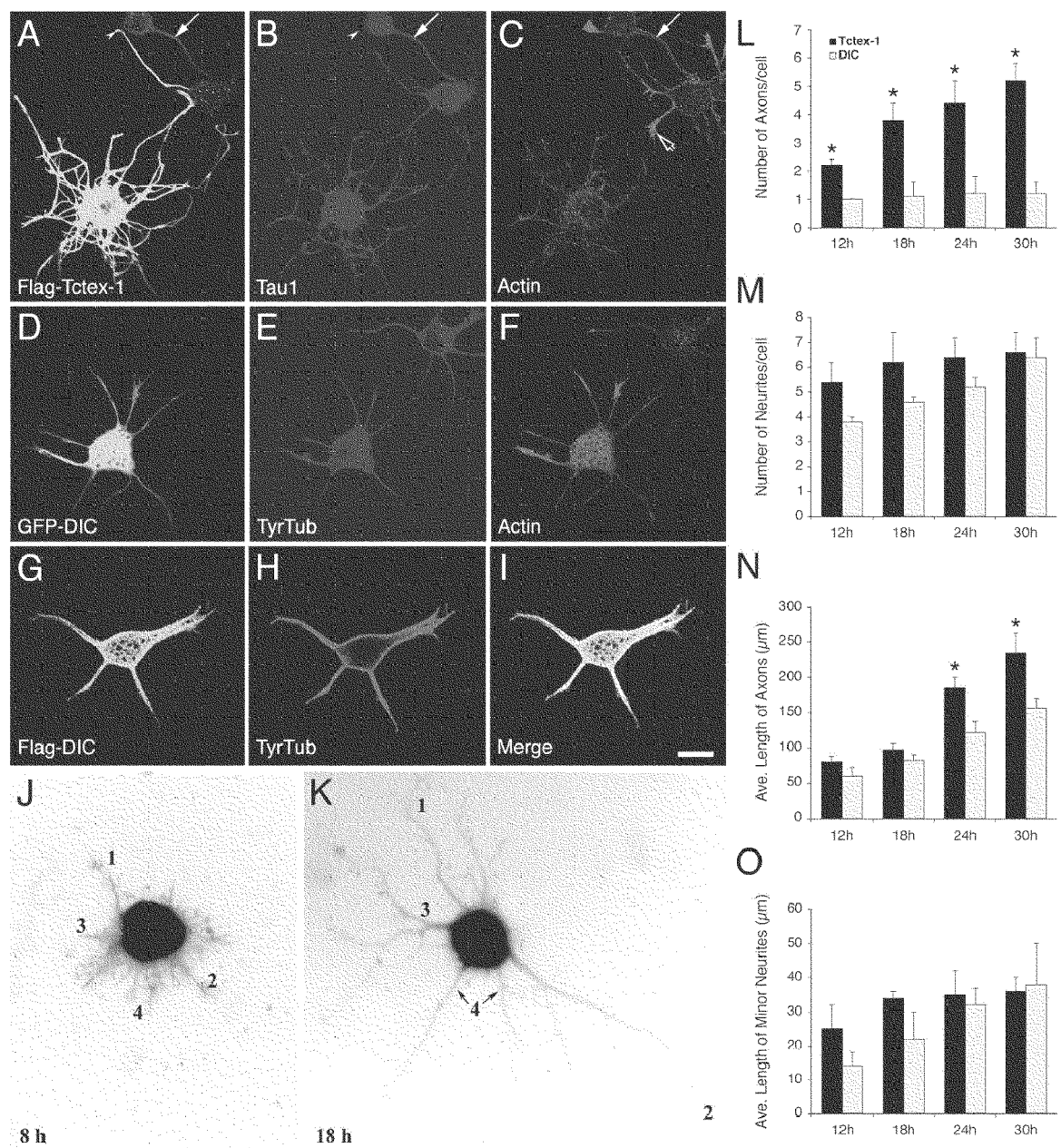
Figures 3A-O

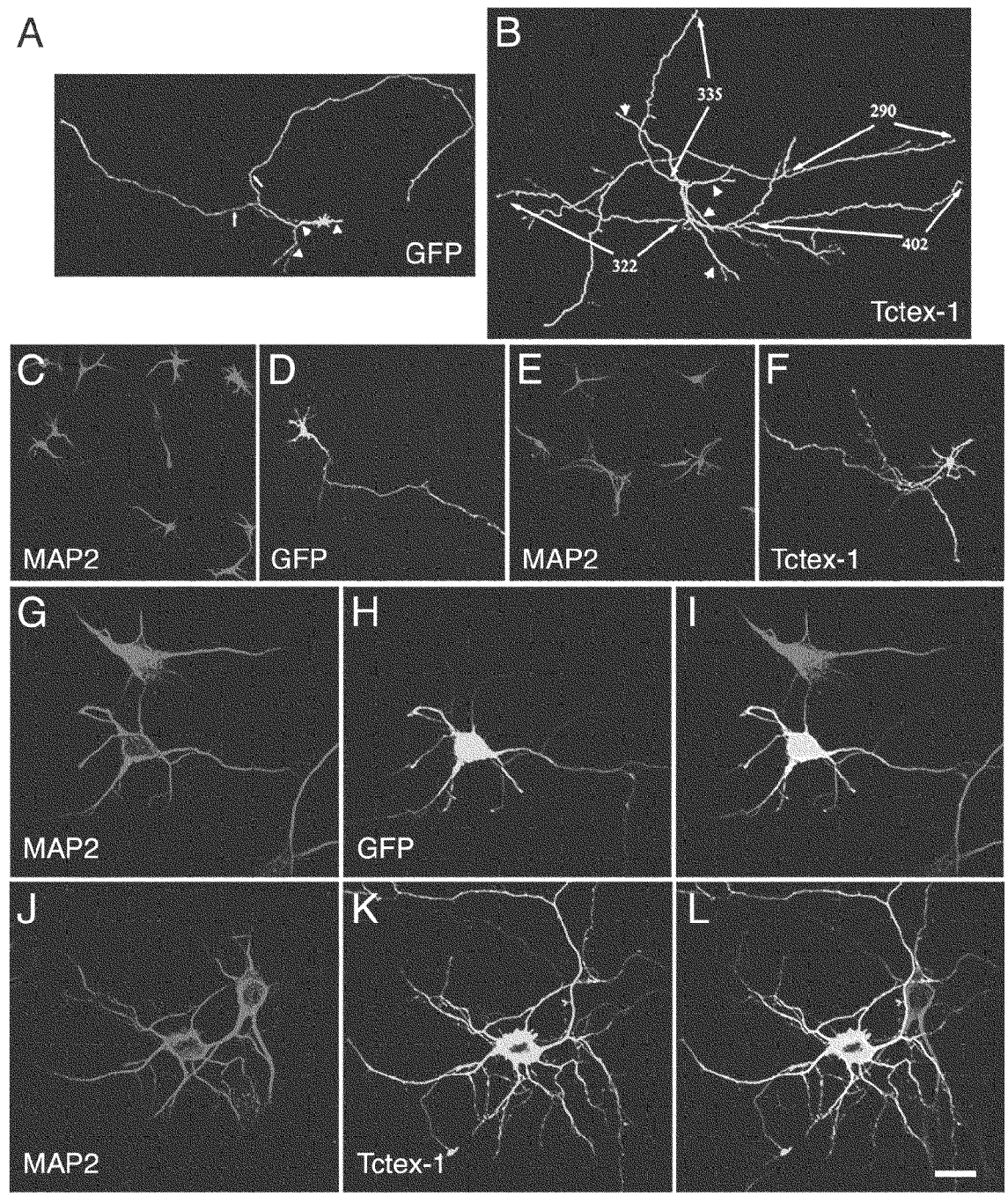
Figures 4A-L

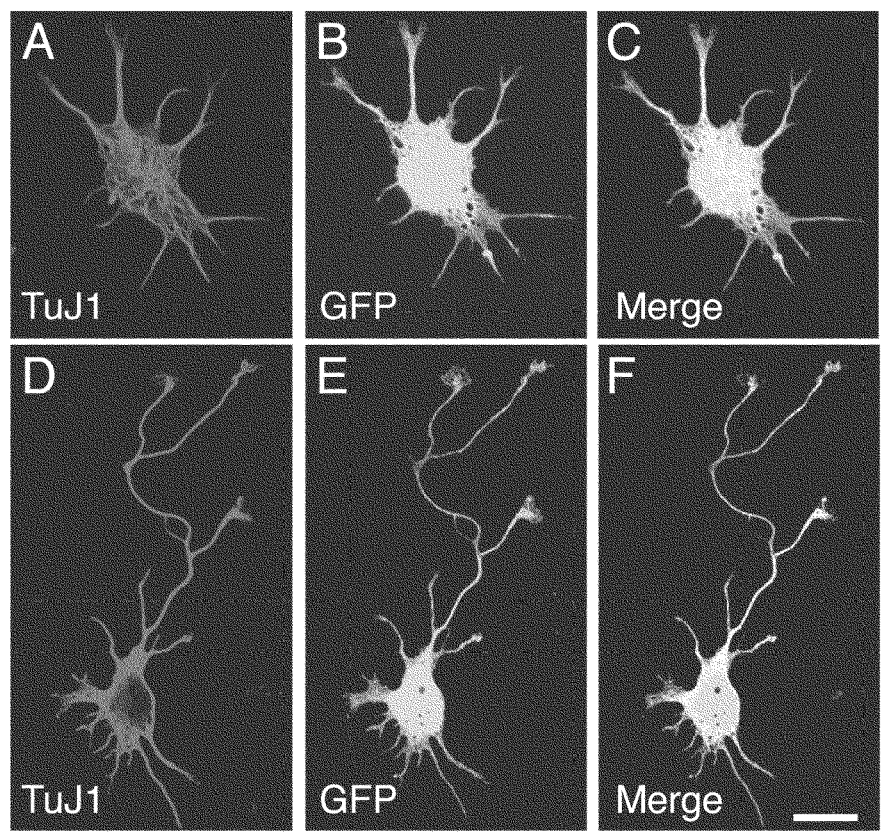
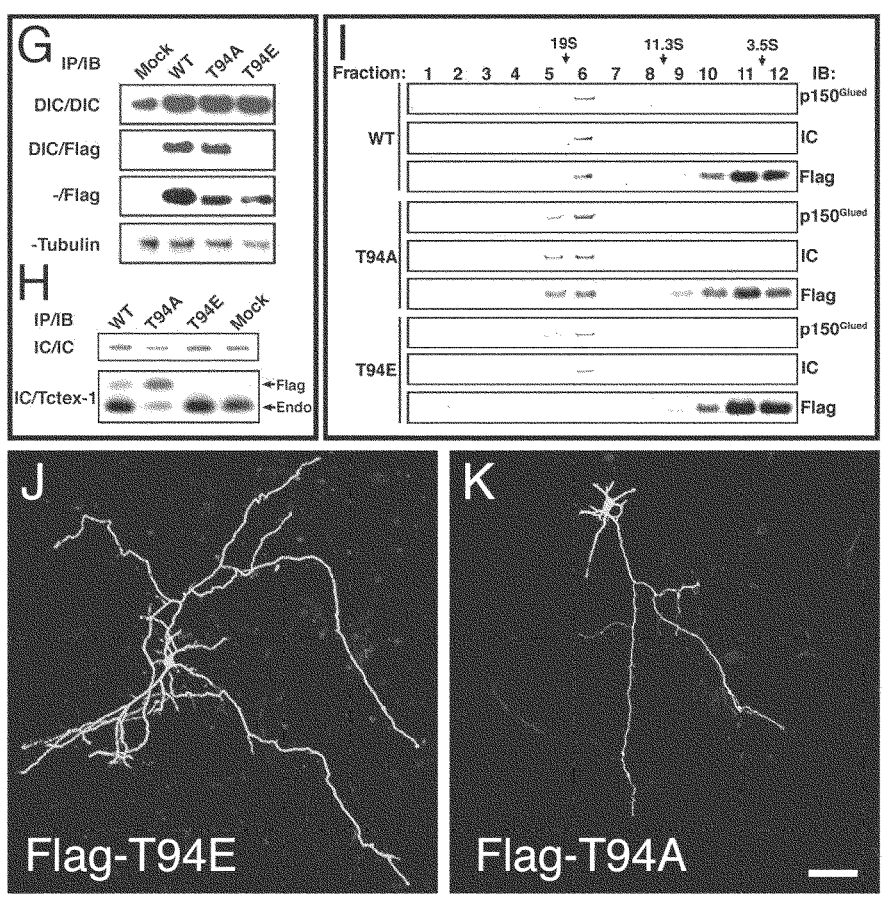
Figures 5A-K

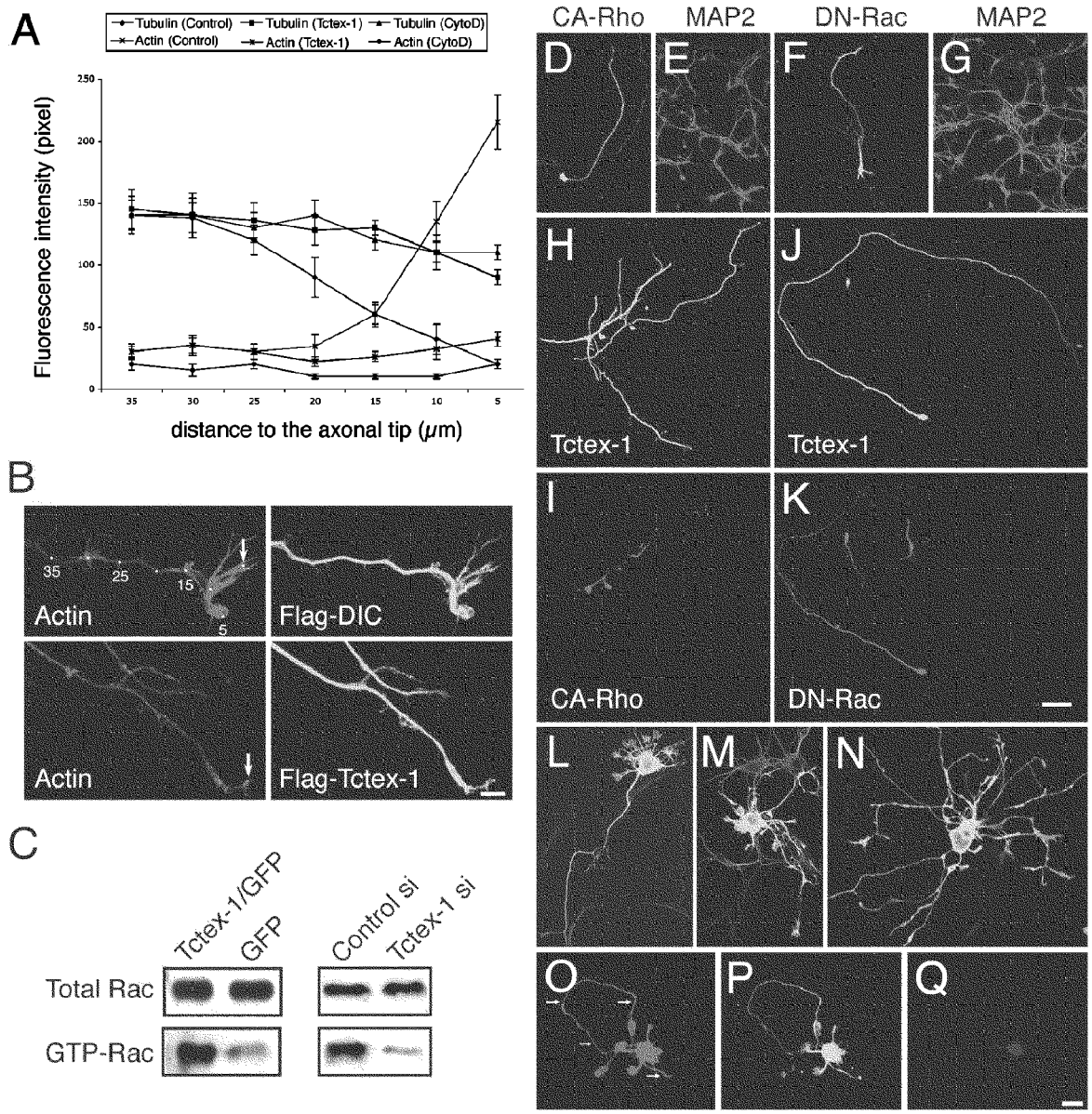
Figures 6A-Q

FIGURE 7 - 1
Wildtype Tctex-1 Protein and Nucleotide Sequences from Various Organisms NP_777045 (protein sequence for t-complex-associated-testis-expressed 1-like
1 from Bos taurus) SEQ ID NO:1: MEDYQAAEET AFVVDEVSNI VKEAIESAIG GNAYQHSKVN
QWTTNVVEQT LSQLTKLGKP FKYIVTCVIM QKNGAGLHTA SSCFWDSSTD GSCTVRWENK TMYCIVSAFG
LSI NM_174620 (nucleotide sequence encoding t-complex-associated-testis-expressed
1-like 1 from Bos taurus) SEQ ID NO: 2 GGCACGAGCG GCGACGCGCG GGCGGCAAGA
TGGAAGACTA CCAGGCCGCC GAGGAGACTG CTTTTGTTGT TGATGAAGTG AGCAACATCG TAAAAGAGGC
CATAGAAAGC GCCATCGGTG GCAACGCCTA TCAGCACAGC AAAGTCAATC AGTGGACCAC AAACGTAGTG
GAGCAGACCT TAAGCCAACT CACCAAGCTG GGGAAGCCAT TTAAGTACAT CGTGACCTGT GTGATCATGC
AGAAGAATGG AGCGGGCCTG CACACGGCAA GCTCGTGCTT CTGGGACAGC TCCACCGATG GGAGCTGCAC
CGTGCGATGG GAGAACAAGA CCATGTACTG CATCGTCAGC GCCTTCGGCC TGTCCATCTG ACAGCCGCCC
CGCCCGACCT CTCTCCTTCC ACCACATCCC TTCTCTCCCA TCTTCTAACA CCGACCGGCT ATACAGCGAT
CTCCTTTCTC ATCCAAAGTG TGTTTTTGTG GCACTCTCAA CATGTAGAGA AAAAAACAAA TAACCACACT
GCTCCTCTGT GACCTGCACA CCAAGTCAGA GGCGTCGTCA CCGCAGGTAG CAGGAGCCTG TCCTGCCGCT
TGTCTTAACT CTGAATGTTT CTTCTCAAAG GTGCTAAAAG CCGAAATCTG CTAGTGTGAA ACTTTCTCTA
CTCTCTGAAA CGAATCAAAT ACACTAATTT TCCATACTTT GTACTTTTTG TTAGAATAAT AAATTATTAA
GATTTAAAAA AAAAAAAAAA AAAAAAAA CAI95303 (protein sequence for t-complex-associated-testis-expressed 1-like 1
from Homo sapiens)
SEQ ID NO: 3: MEDYQAAEET AFVVDEVSNI VKEAIESAIG GNAYQHSKVN QWTTNVVEQT
LSQLTKLGKP FKYIVTCVIM QKNGAGLHTA SSCFWDSSTD GSCTVRWENK TMYCIVSAFG LSI CAI95303 (nucleotide sequence encoding t-complex-associated-testis-expressed
1-like 1 from Homo sapiens)
SEQ ID NO: 4: ATGGAAGACT ACCAGGCTGC GGAGGAGACT GCTTTTGTTG TTGATGAAGT
GAGCAACATT GTAAAAGAGG CTATAGAAAG CGCAATTGGT GGTAACGCTT ATCAACACAG CAAAGTGAAC
CAGTGGACCA CAAATGTAGT AGAACAAACT TTAAGCCAAC TCACCAAGCT GGGAAAACCA
TTTAAATACA TCGTGACCTG TGTAATTATG CAGAAGAATG GAGCTGGATT ACACACAGCA
AGTTCCTGCT TCTGGGACAG CTCTACTGAC GGGAGCTGCA CTGTGCGATG GGAGAATAAG
ACCATGTACT GCATCGTCAG TGCCTTCGGA CTGTCTATTT AA NP_112608 (protein sequence for t-complex-associated-testis-expressed 1-like
1 from Rattus norvegicus)
SEQ ID NO:5: MEDFQASEET AFVVDEVSNI VKEAIESAIG GNAYQHSKVN QWTTNVVEQT
LSQLTKLGKP FKYIVTCVIM QKNGAGLHTA SSCFWDSSTD GSCTVRWENK TMYCIVSAFG LSI NP_112608 (nucleotide sequence encoding t-complex-associated-testis-expressed
1-like 1 from Rattus norvegicus)
SEQ ID NO: 6: GCGCTAGAGG GAAGATGGAA GACTTCCAGG CCTCCGAGGA GACTGCATTT
GTTGTGGATG AAGTGAGCAA CATTGTAAAG GAGGCTATAG AAAGTGCCAT CGGCGGTAAC GCCTACCAGC
ACAGCAAAGT CAACCAGTGG ACCACTAATG TTGTAGAACA GACTTTGAGC CAACTCACCA AACTGGGGAA
ACCATTTAAA TACATTGTGA CCTGTGTGAT CATGCAGAAG AATGGTGCTG GGTTACACAC CGCAAGTTCC
TGCTTCTGGG ACAGCTCCAC GGACGGGAGC TGCACAGTCC GATGGGAGAA CAAGACCATG TACTGCATCG
TCAGTGCCTT CGGACTGTCC ATCTGACCGC CTGACTGCCT CAGCCTCCGG TTCCAGCGTT TCTAGTCCAT
CTTACCACCA GCTATGTTGG GCGGATACCT TCCTCCTCTT TAAGTTGTTC TGAGGCACTC CCAAAATGTA
GAGAAATAAA CCAAATGACC CTGGCCACAG GAACCACACG ACGGACACTA GGCAGATGAG CAGCCACCTG
TCATCCAAGG CAGGCAGTAC CAGTTGTCTT AACTGTCTTC TCAAAGGTGC TAAGATCTCA AGTCTGCTAG
TGGAAACTTC TCTACTTTCT GAAATGATTC AGATACACTA ATTTTCCACA CTTTATACTT TTGTTAGAAT
AATAAATTAT TCAGAATT NP_033368 (protein sequence for t-complex-associated-testis-expressed 1-like
1 from Mus musculus)
SEQ ID NO: 7: MEDFQASEET AFVVDEVSSI VKEAIESAIG GNAYQHSKVN QWTTNVLEQT
LSQLTKLGRP FKYIVTCVIM QKNGAGLHSA SSCFWDSSTD GSCTVRWENK TMYCIVSTFG LSI

FIGURE 7 - 2
Wildtype Tctex-1 Protein and Nucleotide Sequences from Various Organisms NM_009342 (nucleotide sequence encoding t-complex-associated-testis-expressed
1-like 1 from Mus musculus)
SEQ ID NO: 8: TGGTAGTGGT CAGGGTCCCC CGCGCGGGGG CGGAGTGGGC GTGGCCTGAC
CGCGCCTGCG CAGTCCACTC TACTCGGCGG GCGAAGGAGA TGCGTTAAAG ATGGAAGACT TCCAGGCCTC
AGAGGAGACT GCATTTGTTG TTGATGAAGT GAGCAGCATT GTAAAGGAGG CTATAGAAAG CGCCATCGGT
GGTAATGCCT ACCAGCACAG CAAAGTCAAC CAGTGGACCA CTAATGTCCT AGAACAGACT TTGAGCCAAC
TCACCAAACT GGGGAGACCA TTTAAATACA TTGTGACCTG TGTGATCATG CAGAAGAACG GTGCTGGGTT
ACACTCCGCA AGTTCCTGCT TCTGGGACAG CTCCACAGAC GGAAGCTGCA CAGTCCGATG GGAGAACAAG
ACCATGTACT GCATCGTCAG TACCTTCGGA CTGTCCATCT GACCACCTTG CCAGCCTCAG CCTCGTGGTC
CCAGCATTTC CAGTCCATCT TAACCACCAG CTATGTTGGG CAAACCCCTT CCTCCTAAGT TGTTCTGTGG
CACTCTCAAA AAACCAAATG ACTCCCCAGT CACAGGAACC ACATGACTTC AGCCAGATTA GCAGCCACCT
GTCATCTGAG CCAGGCAGTA CCACTTGTCT TAACTGTCTT CTCCAAGGTG CTAAAAACTC AAGTCTGCTG
GTGGAAACAG CTCTACTTTC TGAAATGATT CAGATACACT AACTTTCCAT ACTTTATTCT TTCTTAGAAT
AATAAATTAT TCAAAATTAA AAAAAAAAAA AAAAAAAAA A NP_001011428 (hypothetical protein LOC496911 from Xenopus tropicalis)
SEQ ID NO: 9: MDEFQTAEES SFVVDEISNI IKESIESAIG GNAYQHNKVN QWTTNVVEQT
LSQLTKLGKP FKYIVTCVIM QKNGAGLHTA SSCFWDNATD GSCTVRWENK TMYCIVSAFG LAI NM_001011428 (nucleotide sequence encoding LOC496911 from Xenopus tropicalis)
SEQ ID NO: 10: TGCAGGGTGG CTGCTGGTGC GGACGTTGTT GGTAGTGGGA AAGATGGATG
AATTTCAAAC GGCAGAGGAG TCTTCATTTG TAGTGGATGA AATAAGCAAC ATCATTAAAG AGTCAATTGA
AAGTGCCATC GGTGGTAATG CTTACCAGCA CAACAAAGTG AACCAGTGGA CTACTAATGT GGTAGAACAG
ACACTCAGTC AGCTTACAAA GTTGGGCAAG CCGTTCAAAT ACATAGTGAC CTGTGTAATT ATGCAAAAGA
ATGGTGCAGG ACTTCATACA GCAAGCTCTT GCTTCTGGGA TAATGCAACG GATGGAAGCT GTACCGTGAG
ATGGGAGAAC AAGACTATGT ACTGTATTGT CAGTGCCTTT GGACTTGCAA TATAATTTTT CAATTCCTGA
TTGTTTTTTT ATAAATTCAT ACTCTGACAA CACCTTTTTG AGTTAAAGAA AATTCTTATT TTTTCATCTG
AAAGAATGCT ATTTTTTTTG GCTATTCAGC ATTATAACCA TTAGTACTAA ACCAAATCTA AAATCTTCTG
CATTATCTTA TTTAAGGTGC TACAAGCTAC TATCAAGTGC CACAACAAAT TGCCTGATCT TGTTCATCAA
ATACAATAAT TGTTACATTT GTTACCTTAG CTAATACTAA ATTATTGAAT ACATGCTTTA TATTTTACA
GTGTAATTTC CACTGTGTCA TTGGTTCTAC CTGGCATCCA CCATTTTTCT TCCTGTTTTT TGTCACTGTG
TAAAAACAAA CAAATTAATA TGGCAGATAT ATTTTTAGG ACTAGTCTGT CATTTGTGTC TCAACTTGTT
AATTTTTTTT GCATCACTTT TCATGTGTGC ACTGTCTTAA TATCACAATT TCACTAATAA CTTGTGTTAA
CAGCATGGAT GGGTTTTTTT TAGAATGACC TAATGCAAAG ACTTGTATTT ATGTTGTTAA AAAAATAAAT
GCATGGCAAG AAAAGCATCA AAGGTTTCAG GCTATTTTAG GCAGTTTCAC TGTGCATTGG GAGGTGTGTT
GTACCCAAGG AGAAAATAAA TTTTGCCAGA CTTGAAAAAA AAAAAAAAAA AAAAAAAAAA AAAAA CAA70165 (dynein light chain subunit; tctex-1 from Drosophila melanogaster)
SEQ ID NO: 11: MDDSREESQF IVDDVSKTIK EAIETTIGGN AYQHDKVNNW TGQVVENCLT
VLTKEQKPYK YIVTAMIMQK NGAGLHTASS CYWNNDIDGS CTVRWENKTM YCIVSVFGLA V Y08968(nucleotide sequence encoding dynein light chain subunit; tctex-1 from
Drosophila melanogaster)
SEQ ID NO: 12: CTTAGAAAAA TAGAATCCCG ATATATATTA TTTGGACTGC TCGAACGCCG
CCGACGAGCC CAAAAACGCG CGCACATTTA CAACGACAAC AATACAAACT TGAGCTCAGT ACGTAAACTT
TTTTGACCAG CTGCCGTTAG AAGCAAATCA AAGCTGCGAC GATGGATGAC TCACGCGAAG AAAGCCAGTT
CATTGTGGAC GACGTGAGCA AGACGATTAA AGAGGCCATC GAGACGACCA TCGGCGGTAA CGCCTACCAG
CACGACAAGG TGAACAACTG GACCGGCCAG GTGGTGGAGA ACTGCCTGAC GGTGCTCACC AAGGAGCAGA
AGCCCTACAA GTACATTGTG ACCGCCATGA TCATGCAAAA GAACGGTGCT GGACTCCACA CCGCCAGCTC
CTGCTACTGG AACAACGACA CCGACGGATC GTGCACAGTA CGCTGGGAGA ACAAGACCAT GTACTGCATC
GTTTCGGTCT TCGGACTGGC CGTCTAGAGT GGAGGAATGG CAGGACTGCC GGAATTCGCA TGAAAATGAC
TTAGAAGGGG G

FIGURE 7 - 3
Wildtype Tctex-1 Protein and Nucleotide Sequences from Various Organisms NP_991171 (t-complex-associated-testis-expressed 1-like protein from Danio rerio)
SEQ ID NO: 13: MEEYHSGDEV SFNPDDASNV VKECIEGIIG GVDYSQNKVN QWTASIVEHS
LTQLVKQGKP FKYIVNCAVM QKSGAGLHTA NSCYWDTTTD GSCTVRWENR TMYCVVSVFA VAIAL NM_205608 (t-complex-associated-testis-expressed 1-like protein from Danio rerio)
SEQ ID NO: 14: ACATCAGTCT GTTGTCAGTG AAAGAAAAGA TACAGTCGTC TGAGTTTGCC
GTCCAGATTT TTGGTGTTTT TTAAGCTGAA AAGATGGAGG AGTATCATTC TGGAGATGAA GTTTCTTTCA
ACCCAGATGA TGCAAGTAAT GTTGTAAAGG AGTGCATCGA GGGGATTATT GGTGGTGTGG ACTACAGCCA
GAACAAAGTC AACCAGTGGA CGGCCAGCAT AGTCGAGCAC TCTCTCACTC AGTTAGTCAA ACAAGGCAAA
CCCTTCAAAT ACATTGTCAA CTGTGCTGTG ATGCAGAAAA GCGGCGCAGG TCTTCACACA GCCAACTCTT
GTTATTGGGA CACTACCACT GACGGAAGTT GCACAGTGAG GTGGGAGAAC CGGACTATGT ATTGCGTCGT
CAGTGTGTTT GCAGTGGCCA TTGCACTATG AGCTGAGTCC CACACATGCA CACACACACA CACACACACA
CACACACACT GAAGATCAAA GCCAGCTTCA CTCACATGTC TATTATTAAG CTTTTTGCTT CAACACATCG
GCTTAAACAT CACCCATGTT TAGCTCCTGT CTGTTTGGCC TGATACAATG TTTAGACTGA ATTGTAAGCT
CTTATCTACT ACAATGTATC TATATTTGCT TCTCTGTTTT TGGACCTGCA AAGGTATCAT GCACCTTTGC
TCTGTATAGA ATGAAATGAA AATTTGTTGA TGGTAATTAT TAAAGTAGTT TGTTTTGGGT TAATAATAC
AGTGTTATGA ATTCATCTGA ATGGTTTTTT TTTAGTTTT CAGCCACCAA AGGGCATGCA ACTTTGTTTA
AGCTTGACAT AAAGACAGAG AAATGTAAAA TTATTCACAC ATGATGTACG AATGTCATGT CATGTCATAA
TAGTTGTTCA GCATTATTTT AGGGAATTGA AAATGAGTTT TATCCCCGGC TCTTAAGTTT AAAAACAGCC
AGAACACAAT CATTTTGCTG AAAGATTTAT ACAAGAAAAT GACTTTTGT TTGTTTGTTT GTTTGTTTAT
TTATTCAGTT AATTAACCAC ACACACATTT CCTCTACAAT AATGTTAAAT AATTGAATTG CCAAATCTTA
TTAACATGAA AAACAAGTAC TGGAATTAAA AGCTTTGTTT GATTCACTAA AAAAAAAAAA AAAAAAAAA

FIGURE 8
Alignment of Wildtype Tctex-1 From Various Species

```
MEDYQAAEET AFVVDEVSNI VKEAIESAIG GNAYQHSKVN QWTTNVVEQT LSQLTKLGKP FKYIVTCVIM QKNGAGLHTA SSCFWDSSTD GSCTVRWENK TMYCIVSAFG LSI
(BOVINE)

MEDYQAAEET AFVVDEVSNI VKEAIESAIG GNAYQHSKVN QWTTNVVEQT LSQLTKLGKP FKYIVTCVIM QKNGAGLHTA SSCFWDSSTD GSCTVRWENK TMYCIVSAFG LSI
(HUMAN)

MEDFQASEET AFVVDEVSNI VKEAIESAIG GNAYQHSKVN QWTTNVVEQT LSQLTKLGKP FKYIVTCVIM QKNGAGLHTA SSCFWDSSTD GSCTVRWENK TMYCIVSAFG LSI
(RAT)

MEDFQASEET AFVVDEVSSI VKEAIESAIG GNAYQHSKVN QWTTNVLEQT LSQLTKLGRP FKYIVTCVIM QKNGAGLHSA SSCFWDSSTD GSCTVRWENK TMYCIVSTFG LSI
(MOUSE)

MDEFQTAEES SFVVDEISNI IKESIESAIG GNAYQHNKVN QWTTNVVEQT LSQLTKLGKP FKYIVTCVIM QKNGAGLHTA SSCFWDNATD GSCTVRWENK TMYCIVSAFG LAI
(FROG)

MEEYHSGDEV SFNPDDASNV VKECIEGIIG GVDYSQNKVN QWTASIVEHS LTQLVKQGKP FKYIVNCAVM QKSGAGLHTA NSCYWDTTTD GSCTVRWENR TMYCVVSVFA VAIAL
(ZEBRA FISH)

MDDSREES QFIVDDVSKT IKEAIETTIG GNAYQHDKVN NWTGQVVENC LTVLTKEQKP YKYIVTAMIMQ KNGAGLHTA SSCYWNNDTD GSCTVRWENK TMYCIVSVFG LA V
(FRUIT FLY)
```

FIGURE 9 - 1
Wildtype RP3 Protein and Nucleotide Sequences from Various Organisms NP_006511 (protein sequence for t-complex-associated-testis-expressed 1-like from Homo sapiens)
SEQ ID NO: 18:
MEEYHRHCDE VGFNAEEAHN IVKECVDGVL GGEDYNHNNI NQWTASIVEQ SLTHLVKLGK AYKYIVTCAV
VQKSAYGFHT ASSCFWDTTS DGTCTVRWEN RTMNCIVNVF AIAIVL NM_006520 (nucleotide sequence encoding t-complex-associated-testis-expressed 1-like 1 from Homo sapiens)
SEQ ID NO: 19:
ATGGAGGAGT ACCATCGCCA CTGCGACGAG GTTGGCTTCA ATGCTGAGGA AGCCCACAAT
ATTGTCAAAG AGTGTGTAGA TGGGGTTTTA GGTGGTGAAG ATTATAATCA CAACAACATC
AACCAGTGGA CTGCAAGCAT AGTGGAACAA TCCTTAACAC ACCTGGTTAA GTTGGGAAAA
GCCTATAAAT ATATTGTGAC CTGTGCAGTG GTCCAGAAGA GCGCATATGG CTTTCACACA
GCCAGCTCCT GTTTTTGGGA TACCACATCT GATGGAACCT GTACCGTAAG ATGGGAGAAC
CGGACCATGA ACTGTATTGT CAACGTTTTT GCCATTGCTA TTGTTCTTTA A CAI29708 (protein sequence from Pongo pygmaeus)
SEQ ID NO: 20:
MEEYHRHCDE VGFNAEEAHN IVKECVDGVL GGEDYNHNNI NQWTASIVEQ SLTHLVKLGK
AYKYIVTCAV VQKSAYGFHT ASSCFWDTTS DGTCTVRWEN RTMNCIVNVF AIAIVL CR926081 (nucleotide sequence from clone DKFZp459K0610 from Pongo pygmaeus)
SEQ ID NO: 21:
ATGGAGGAGT ACCATCGCCA CTGCGACGAG GTTGGCTTCA ATGCTGAGGA AGCCCACAAT
ATTGTCAAAG AGTGTGTAGA TGGGGTTTTA GGTGGTGAAG ATTATAATCA CAACAACATC
AACCAGTGGA CCGCAAGCAT AGTGGAACAA TCCTTAACAC ATCTGGTTAA GTTGGGAAAA
GCTTATAAAT ATATTGTGAC CTGTGCAGTG GTCCAGAAGA GCGCATATGG CTTTCACACA
GCCAGCTCCT GTTTTTGGGA TACCACATCT GATGGAACCT GTACCGTAAG ATGGGAGAAC
CGGACCATGA ACTGTATTGT CAATGTTTTT GCCATTGCTA TTGTTCTTTA A NP_001003001 (protein sequence for t-complex-associated-testis-expressed 1-like from Canis familiaris)
SEQ ID NO: 22:
MEEYHRHCDE VGFNADEAHN IVKECIDGVL GGEDYNQNNI NQWTASIVEQ SLTHLVKLGK
AYKYIVTCAV VQRSAYGFHT ASSCFWDTTS DGTCTVRWEN RTMNCIVNVF AIAIVL NM_001003001 (nucleotide sequence for Canis familiaris t-complex-associated-testis-expressed 1-like)
SEQ ID NO: 23:
ATGGAGGAGT ACCACAGGCA CTGCGACGAG GTTGGCTTCA ATGCTGATGA AGCTCACAAT
ATTGTGAAGG AGTGTATAGA TGGGGTCTTG GGTGGTGAAG ATTATAACCA GAACAACATC
AACCAATGGA CTGCAAGCAT AGTGGAACAA TCCTTAACAC ATTTGGTTAA GTTGGGAAAA
GCTTATAAAT ATATTGTGAC CTGTGCAGTG GTCCAGAGGA GTGCCTATGG CTTTCACACA
GCCAGCTCAT GTTTTTGGGA CACCACATCT GATGGAACCT GTACCGTAAG ATGGGAGAAC
CGAACCATGA ACTGTATTGT CAATGTTTTT GCCATTGCTA TTGTTCTGTG A NP_001009762 (protein sequence for T-complex associated-testis-expressed 1-like from Ovis aries)
SEQ ID NO: 24:
MEEYHRPCDE VGFNADEAHN IVKECIDGVL GGEDYNQNNI NQWTASIVEQ SLAHLVKLGK
AYKYIVTCAV VQRSPYGFHT ASSCFWDTTS DGTCTVRWEN RTMNCIVNVF AIAIVL

FIGURE 9 - 2
Wildtype RP3 Protein and Nucleotide Sequences from Various Organisms

```
NM_001009762 (nucleotide sequence for Ovis aries T-complex associated-testis-
expressed 1-like)
SEQ ID NO: 25:
ATGGAGGAGT ACCATCGCCC CTGCGACGAG GTTGGCTTCA ATGCTGATGA AGCCCACAAT
ATTGTTAAAG AGTGTATAGA TGGGGTCTTG GGAGGTGAAG ATTATAATCA GAACAATATC
AACCAATGGA CTGCAAGCAT AGTGGAACAA TCCCTAGCAC ATCTGGTTAA GCTGGGAAAA
GCTTATAAGT ATATTGTGAC CTGTGCCGTG GTCCAGAGGA GTCCATATGG CTTTCACACA
GCCAGCTCAT GTTTTGGGA CACCACATCT GATGGAACCT GCACTGTAAG ATGGGAGAAC
CGAACCATGA ACTGTATCGT CAATGTTTTT GCCATTGCTA TTGTCCTGTA G NP_080251 (protein sequence for t-complex-associated-testis-expressed 1-like
Mus musculus)
SEQ ID NO: 26:
MEGYQRPCDE VGFNADEAHN IVKECVDGVL GGNDYNENNI NQWTASIVEQ SITHLVKLGK
AYKYIVTCAV VQRSPYGFHT ASSCFWDTTS DGTCTIRWEN RTMNCIVNVF AVAIVL NM_025975 (nucleotide sequence for Mus musculus t-complex-associated-testis-
expressed 1-like)
SEQ ID NO: 27:
ATGGAGGGGT ACCAACGGCC CTGCGATGAG GTTGGCTTCA ATGCTGATGA AGCCCATAAT
ATAGTCAAAG AGTGTGTTGA TGGAGTTTTG GGTGGTAACG ATTATAATGA GAATAACATC
AACCAATGGA CTGCAAGCAT AGTGGAACAG TCTATAACAC ATTTGGTCAA ACTGGGGAAA
GCTTACAAGT ACATTGTGAC CTGTGCAGTG GTCCAGAGGA GCCCGTATGG ATTTCACACA
GCCAGCTCCT GTTTTGGGA TACAACATCT GATGGAACCT GTACCATCAG ATGGGAGAAC
CGTACCATGA ACTGCATCGT GAATGTTTTT GCAGTTGCGA TTGTCCTGTA G NP_001013246 (protein sequence for T-complex associated-testis-expressed 1-
like from Rattus norvegicus)
SEQ ID NO: 28:
MDGYQRPCDE IGFNAEEAHN IVKECVEGVL GGNDYNQNSI NQWTASIVEQ SIAHLVKLGK
AYKYIVTCAV VQRSPYGFHV ASSCFWDTTS DGTCTVRWEN RTMNCVVNVF AVAIVL NM_001013228 (nucleotide sequence for Rattus norvegicus T-complex associated-
testis-expressed 1-like)
SEQ ID NO: 29:
ATGGACGGGT ACCAGCGGCC CTGCGACGAG ATTGGCTTCA ATGCTGAGGA AGCACATAAT
ATAGTCAAAG AGTGTGTTGA AGGAGTCTTG GGTGGTAATG ACTATAACCA GAATAGCATC
AACCAGTGGA CCGCAAGCAT CGTTGAACAA TCTATAGCTC ATTTGGTCAA ACTGGGGAAA
GCTTACAAGT ACATCGTGAC CTGTGCAGTA GTCCAGAGGA GCCCATATGG ATTTCACGTG
GCCAGCTCCT GTTTTGGGA TACAACATCT GATGGCACCT GTACCGTTAG ATGGGAGAAT
CGAACCATGA ACTGCGTTGT TAATGTTTTT GCAGTAGCAA TTGTCCTATA A
```

FIGURE 9 - 3
Wildtype RP3 Protein and Nucleotide Sequences from Various Organisms

NP_991171 (protein sequence for t-complex-associated-testis-expressed 1-like from Danio rerio)
SEQ ID NO: 30:
MEEYHSGDEV SFNPDDASNV VKECIEGIIG GVDYSQNKVN QWTASIVEHS LTQLVKQGKP
FKYIVNCAVM QKSGAGLHTA NSCYWDTTTD GSCTVRWENR TMYCVVSVFA VAIAL NM_205608 (nucleotide sequence for Danio rerio t-complex-associated-testis-expressed 1-like)
SEQ ID NO: 31:
ATGGAGGAGT ATCATTCTGG AGATGAAGTT TCTTTCAACC CAGATGATGC AAGTAATGTT
GTAAAGGAGT GCATCGAGGG GATTATTGGT GGTGTGGACT ACAGCCAGAA CAAAGTCAAC
CAGTGGACGG CCAGCATAGT CGAGCACTCT CTCACTCAGT TAGTCAAACA AGGCAAACCC
TTCAAATACA TTGTCAACTG TGCTGTGATG CAGAAAAGCG GCGCAGGTCT TCACACAGCC
AACTCTTGTT ATTGGGACAC TACCACTGAC GGAAGTTGCA CAGTGAGGTG GGAGAACCGG
ACTATGTATT GCGTCGTCAG TGTGTTTGCA GTGGCCATTG CACTATGA

FIGURE 10
Alignment of Wildtype RP3 From Various Species

```
MEEYHRHCDE VGFNAEEAHN IVKECVDGVL GGEDYNHNNI NQWTASIVEQ SLTHLVKLGK AYKYIVTCAV VQKSAYGFHT ASSCFWDTTS DGTCTVRWEN RTMNCIVNVF AIAIVL
(HUMAN)

MEEYHRHCDE VGFNAEEAHN IVKECVDGVL GGEDYNHNNI NQWTASIVEQ SLTHLVKLGK AYKYIVTCAV VQKSAYGFHT ASSCFWDTTS DGTCTVRWEN RTMNCIVNVF AIAIVL
(ORANGUTAN)

MEEYHRHCDE VGFNADEAHN IVKECIDGVL GGEDYNQNNI NQWTASIVEQ SLTHLVKLGK AYKYIVTCAV VQRSAYGFHT ASSCFWDTTS DGTCTVRWEN RTMNCIVNVF AIAIVL
(DOG)

MEEYHRPCDE VGFNADEAHN IVKECIDGVL GGEDYNQNNI NQWTASIVEQ SLAHLVKLGK AYKYIVTCAV VQRSPYGFHT ASSCFWDTTS DGTCTVRWEN RTMNCIVNVF AIAIVL
(SHEEP)

MEGYQRPCDE VGFNADEAHN IVKECVDGVL GGNDYNENNI NQWTASIVEQ SITHLVKLGK AYKYIVTCAV VQRSPYGFHT ASSCFWDTTS DGTCTIRWEN RTMNCIVNVF AVAIVL
(MOUSE)

MDGYQRPCDE IGFNAEEAHN IVKECVEGVL GGNDYNQNSI NQWTASIVEQ SIAHLVKLGK AYKYIVTCAV VQRSPYGFHV ASSCFWDTTS DGTCTVRWEN RTMNCVVNVF AVAIVL
(RAT)

MEEYH SGDE VSFNPDDASN VVKECIEGII GGVDYSQNKV NQWTASIVEH SLTQLVKQGK PFKYIVNCAV MQKSGAGLHT ANSCYWDTTT DGSCTVRWEN RTMYCVVSVF AVAIAL
(ZEBRAFISH)
```

TCTEX-1-RELATED POLYPEPTIDES

CROSS-REFERENCE TO RELATED APPLICATION

This application claims the benefit of U.S. Provisional Application No. 60/696,205, filed Jul. 1, 2005, which is hereby incorporated herein by this reference.

STATEMENT OF GOVERNMENT INTEREST

The disclosed subject matter was developed with support from the National Institutes of Health under Grant No. 5R01EY011307. The U.S. government may have certain rights in the disclosed subject matter.

BACKGROUND

Most tissues, such as muscle, skin, and liver, have the ability to repair and regrow after an injury. However, the brain, spinal cord and other nervous system tissues are very limited in their ability to repair and regrow. Neurons, which comprise nervous system tissue, become assembled into functional networks by growing out axons and dendrites, collectively called neurites. They connect synaptically to other neurons, and are critical for communication between each other. Understanding neurite outgrowth is important to nervous system research, because compounds that promote neurite outgrowth have potential curative effects in nervous systems disorders such as stroke, Alzheimer's disease, Parkinson's disease and spinal cord injury.

SUMMARY

Provided herein, among other things, are novel Tctex-1 polypeptides and compositions thereof that are capable of stimulating neurite growth (neuritogenesis) and/or neuronal progenitor proliferation (neurogenesis), as well as nucleic acids, vectors, host cells, etc. for expression and production of the same. The Tctex-1 polypeptides are small, about 14 kDa or less, and are capable of being fused with other proteins, e.g., as delivery agents, thus making them suitable for relatively easy administration as a therapeutic agent for nervous system disorders. Further, provided are novel methods of treating nervous system disorders using the Tctex-1 polypeptides and compositions thereof, optionally in conjunction with other modes of therapy or stimulation (such as robotic devices), as well as kits for the practice of the same.

In an embodiment, a polypeptide may include an amino acid sequence having at least about 95% identity to the amino acid sequence of SEQ ID NO: 42, wherein a residue at position 94 of the polypeptide is an amino acid other than threonine, and wherein the polypeptide stimulates neurite outgrowth or neurogenesis. The residue at position 94 of the polypeptide may be glutamate, or it may be aspartate. A residue at position 82 of the polypeptide may be serine, or it may be an amino acid other than serine. The residue at position 82 of the polypeptide may be glutamate, or it may be aspartate.

In an embodiment, a polypeptide may include an amino acid sequence having at least about 95% identity to the amino acid sequence of SEQ ID NO: 42, wherein a residue at position 82 of the polypeptide is an amino acid other than serine, and wherein the polypeptide stimulates neurite outgrowth or neurogenesis. The residue at position 82 of the polypeptide may be glutamate, or it may be aspartate. A residue at position 94 of the polypeptide may be threonine, or it may be an amino acid other than threonine.

In an embodiment, a polypeptide may include at least the first 14 residues and at most the first 92 residues of an amino acid sequence starting with residue 1 of, and having at least about 95% identity to, the amino acid sequence of SEQ ID NO: 1, 3, 5, 7, 9, 11, 13, 15, 16, or 17, wherein the polypeptide stimulates neurite outgrowth or neurogenesis. The polypeptide may encompass at most the first 71 resides, or the first 54 residues, or the first 14 residues, of an amino acid sequence starting with residue 1 of, and having at least about 95% identity to, the amino acid sequence of SEQ ID NO: 1, 3, 5, 7, 9, 11, 13, 15, 16, or 17.

Nucleic acids may encode any of the aforementioned polypeptides. Vectors may include one or more of the nucleic acids. A host cell, such as an embryonic stem cell, may include one or more of the vectors.

A method of stimulating neurite outgrowth or neurogenesis in a subject may include administering to the subject a pharmaceutical composition that includes any of the aforementioned polypeptides, nucleic acids, vectors, host cells, and/or embryonic stem cells. The method may further include administering a second therapy, such as physical therapy and/or robotic therapy.

BRIEF DESCRIPTION OF THE DRAWINGS

FIGS. 1A-H depict the asymmetric distribution of Tctex-1 in hippocampal neurons. FIGS. 1A-C depict a stage 2-3 neuron immunostained for Tctex-1 (A), tyr-tubulin (B), and F-actin (C). Arrows point to the neurite of the future axon, and open arrows point to the axonal growth cones. FIGS. D and E depict magnified views of axonal growth cones shown in (A) and (C). Arrowheads indicate the co-distributed Tctex-1 and F-actin at the growth cone lamellipodia. Overlay was shown in the insert. FIGS. F and G depict confocal images of a stage 3 neuron co-labeled for Tctex-1 (F), tyr-tubulin (blue in G), and F-actin (red in G). Arrow marks the axon growth cone. FIG. H depicts the quantification of Tctex-1 expression levels in the neurites and growth cones of stage 2-3 neurons. The Tctex-1 labeling index represents the ratio of Tctex-1 labeling intensity relative to the tyr-tubulin labeling intensity. Both the minor neurites and the axonal neurites of these cells were subdivided into three even parts, which were designated as immediate segment (IS), middle segment (MS), and distal segment (DS), according to their distance from the cell body. The Tctex-1 labeling in the central regions (CR) of growth cones (GC) was also considered for quantification. However, the Tctex-1 labeling index in the peripheral regions of growth cones was not shown, because the tyr-tubulin labeling in these regions was often undetectable. n>100. Bars=10 µm (A-C, F, G); 5 µm (D, E).

FIGS. 2A-N depict various data showing that Tctex-1 suppression inhibits neurite outgrowth FIGS. 2A-C depict confocal images of neurons treated with a control AS for 24 h (A), Tctex-1-AS for 24 h (B) or Tctex-1-AS for 36 h (C), followed by immunostaining for tyr-tubulin (red) and F-actin (green). The cell in (A) has the morphological appearance of stage 2-3 cell. In FIG. 2C, the arrow points to a segmented lamellipodium, and the arrowheads point to the short tubulin$^+$ processes that penetrate the lamellipodial veil. FIG. 2D is a chart showing the percentage of cells at stage 1, 2, and 3 of neuritic development after a 24 h or 36 h treatment with control (C) or Tctex-1 AS-oligonucleotides. The scoring of stage 2 and stage 3 cells in control experiments were based on their typical morphological features (Dotti, C. G., et al. (1988). J Neurosci 8, 1454-1468; Goslin, K., and Banker, G. (1991). Rat hippocampal neurons in low density culture. (Cambridge, Mass., MIT)). However, for the purpose of quantification, AS treated cells carrying multiple tubulin+ processes with lengths similar to either minor neurites or axonal neurites were considered for classification, in spite of the fact that most of these processes are not typical neurites and lack growth cones. FIGS. 2E and F depict immunoblotting of equal amounts of proteins extracted from neurons treated with (+) or without (−) AS for 24 h (E) or neurons transfected with control-siRNA/GFP or Tctex-1-siRNA/GFP (F) for 36 h. The indicated antibodies were used. FIGS. 2G-J depict neurons transfected with Tctex-1-siRNA/GFP 2 h after plating and followed by immunostaining for TuJ1 (red) and Tctex-1 (blue) 22 h later. GFP was visualized directly. FIGS. 2K-N depict an example of a typical neuron transfected with Tctex-1-siRNA/GFP ~15 h after plating and immunolabeled 20 h later. The cell has a weak Tctex-1 signal (blue) and a normal level of TuJ1 (red); it was arrested at stage 2 of neuritic development. Bar=10 μm.

FIGS. 3A-O depict data showing that Tctex-1 overexpression caused multiple long axons in hippocampal cultures. FIGS. 3A-C: Dissociated neurons were transfected with Flag-Tctex-1 right before plating. Cells fixed 24 h post-transfection were immunolabeled for Flag, Tau1, and phalloidin. The Flag-Tctex-1-transfected, TuJ1-labeled neurons exhibited abnormally long neurites, and more than one are Tau1+, whereas the nontransfected cells had one single Tau1+ axon (arrow). Arrowheads indicated that a Tau1+ long neurites traveled long distances in and out of the focal plane. Note that cells ectopically expressing Tctex-1 consistently had much weaker labeling for phalloidin, particularly in the neurite tips. Open arrow points to the abundant phalloidin labeling at the neurite tips of untransfected neurons. FIGS. 3D-I: Neurons transfected with GFP-DIC (D-F) or Flag-DIC (G-I) were immunolabeled as indicated 18 h after transfection. Bar=10 μm. FIGS. 3J, K depict time lapse images of a live neuron co-transfected with GFP and Flag-Tctex-1 and imaged at 8 and 18 h after plating. The numbers indicate neurites that elongated during the period of imaging. FIGS. 3L-O depict histograms displaying the morphological analyses of cultures co-transfected with GFP/Flag-Tctex-1 or GFP/Flag-DIC (2 μg each) 2 h after plating and processed for immunolabeling at the indicated time points post-transfection. A neurite that is Tau1+ and ≧50 μm is considered to be an axon. N=50-75 cells per condition. (*p<0.05).

FIGS. 4A-L depict data showing that Tctex-1 regulates both axon and dendrite morphology in older neuronal cultures. Cultures at 3 DIV were transfected with either GFP (2 μg; A, C, D, G-I) or Flag-Tctex-1 (2 μg in B, E, F, J-L) for 18 h before processing. Neurons were either directly visualized for GFP (A, D, H), or immunolabeled for Flag (B, F, K), or MAP2 (C, E, G. J). Arrows and arrowheads in (A) and (B) pointed to axons and dendrites, respectively, based on their morphological features. The numbers in B correspond to the length of axonal processes. Bars=40 μm (A-F); 10 μm (G-L).

FIGS. 5A-K depict data showing that Tctex-1's neuritic effect is dynein-independent. FIGS. 5A-F depict confocal images of 1 DIV neurons co-transfected with DHC-siRNA and GFP 2 h after plating. The GFP+ targeted, TuJ1+ neurons were capable of reaching stage 2 (A-C) or 3 (D-F) of neuritic development. FIG. 5G depicts immunoblots of the DIC immunoprecipitates obtained from mock transfected 293T cells or 293T transfected with either Flag-WT, T94A, or T94E for either DIC or Flag. Total inputs are also shown. FIG. 5H: The DIC immunoprecipitates obtained from the 20S fractions of (I) were immunoblotted with anti-DIC and anti-Tctex-1 Abs. Tctex-1 Ab recognized both Flag-tagged and endogenous (Endo) Tctex-1, which migrated differently. FIG. 5I: Lysates of 293T cells transfected with the either Flag-WT, T94A, or T94E were sedimented in a 5-20% linear sucrose gradient. Each fraction was analyzed by SDS-PAGE and immunoblotted with indicated Abs. FIGS. 5J,K depict immunolabeling of 4 DIV neurons transfected with Flag-T94E and Flag-T94A using anti-Flag Ab. Bars=10 μm.

FIGS. 6A-Q depict data indicating that Tctex-1 regulates the actin cytoskeleton by modulating RhoGTPase. FIG. 6A depicts quantification of F-actin and tubulin fluorescence intensity at the neuritic tip of 1 DIV control neurons, neurons transfected with Flag-Tctex-1, or neurons treated with cytochalasin D (0.5 μg/ml) for 6 h. Measurements were performed pixel by pixel (y axis) along the distal end of axonal processes (x axis). Values of representative measurements taken at 5-μm intervals are shown in the graph. Each value represents the mean±S.E.M. of at least 50 axonal processes for each experimental condition. FIG. 6B depicts representative images of distal axonal processes of neurons transfected with Flag-DIC and Flag-Tctex-1 and labeled for F-actin and Flag. All images were taken using identical confocal settings to quantify paladin labeling. Arrows mark the axonal tips for the zero points used in the quantification described in (A). FIG. 6C: Equal amounts of protein extracted from 3T3 fibroblasts infected with adenovirus encoding Tctex-1/GFP or GFP (left panel) or neurons transfected with Tctex-1-si/GFP or control-si/GFP (right panel) were subjected to the Rac1 activity assay. A representative immunoblot shows the total and GTP-bound Rac1. FIGS. 6D-K depict DIV neurons singly transfected with either HA-CA-RhoA (D, E) or HA-DN-Rac1 (F, G) or double-transfected with Tctex-1/HA-CA-RhoA (H, I), or Tctex-1/HA-DN-Rac1. (J, K) were immunolabeled for either HA (D, F, I, K) together with MAP2 (E, G) or together with Flag (H, J). FIGS. 6L-N depict confocal images of cultured neurons transfected with 1 μg (L), 2 μg (M), or 4 μg (N) of myc-CA-Rac1 and labeled with anti-myc Ab. FIGS. 6O-Q depict confocal images showing the morphology of a neuron co-transfected with myc-CA-Rac1 and Tctex-1-si/GFP (2 μg each; red: myc; green, GFP; blue, Tctex-1). Note that the transfected neuron, which displays very faint Tctex-1 immunofluorescence, extended a single axon (arrows) and several "veiled" shorter neurites. All cells shown in this figure were transfected 2 h after plating and fixed 24 h later. Bars=10 μm.

FIG. 7 depicts the polypeptide and polynucleotide sequences of Tctex-1 proteins from a variety of organisms.

FIG. 8 depicts an alignment of the polypeptide sequences from the various species listed in FIG. 7, with the protein kinase C consensus sequence underlined and the phosphorylation site in bold (SEQ ID NOS 1, 3, 5, 7, 9, 13, and 11 disclosed respectively, in order of appearance).

FIG. 9 depicts the polypeptide and polynucleotide sequences of Rp3 proteins from a variety of organisms.

FIG. 10 depicts an alignment of the polypeptide sequences from the various species listed in FIG. 9, with the expected phosphorylation sites underlined (SEQ ID NOS 18, 20, 22, 24, 26, 28, and 30 disclosed respectively, in order of appearance).

DETAILED DESCRIPTION

A. Definitions

For convenience, before further description of the present invention, certain terms employed in the specification, examples, and appendant claims are collected here. These definitions should be read in light of the entire disclosure and understood as by a person of skill in the art.

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "disorder of the nervous system" refers to a disturbance of function, structure, or both, of the nervous system resulting from, for example, a genetic or embryonic failure in development or from exogenous factors such as poison, trauma, or disease of the nervous system. For example, nervous system disorders include, but are not limited to, stroke (both acute and chronic), spinal cord injury, traumatic injury to brain and/or spinal cord, multiple sclerosis, amyotrophic lateral sclerosis, the paroxysmal disorders (e.g., the epilepsies), autonomic nervous system dysfunction (e.g., arterial hypertension), movement disorders (e.g., hyperkinetic disorders, dyskinesias (resting tremor), basal ganglia hyperkinetic disorders (e.g., Huntington's chorea, hemiballismus), neuropsychiatric disorders (e.g., mania, psychosis obsessive compulsive disorder, and addiction), Alzheimer's disease, Parkinson's disease, hypothalamic dysfunction (e.g., hyperlactemia), neuropathic pain syndromes, acrodynia, Charcot-Marie-Tooth disease, diabetic neuropathies, nerve compression syndromes, neuralgias, neuromuscular junction diseases, POEMS syndrome, optical nerve injury diseases (e.g., glaucoma) and various retinal degenerative diseases (e.g., retinitis pigmentosa, macular degeneration,).

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators may be screened at one time. The activity of a modulator may be known, unknown or partially known.

The term "neurite" refers to any -process growing out of a neuron. The term neurite as used herein encompasses all such cell processes (including both axon and dendrite) growing out of a neuron.

The term "neurite outgrowth" refers to the process of cells growing out of a neuron, or to the cells comprising an outgrowth from a neuron.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

A "patient," "subject" or "host" to be treated by the subject method may mean either a human or non-human animal.

The phrase "pharmaceutically acceptable" refers to those compositions and dosages thereof within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. The term "pharmaceutically acceptable carrier" refers to a carrier(s) that is "acceptable" in the sense of being compatible with the other ingredients of a composition and not deleterious to the recipient thereof.

Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. Further, fragments can include a sub-fragment of a specific region, which sub-fragment retains a function of the region from which it is derived.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis and mass-spectrometry analysis.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

A "residue that mimics a phosphorylated serine or threonine" refers to any amino acid residue that is not a phosphorylated serine or threonine that functions as the phosphorlyated serine or threonine would in the wildtype protein at the position in which such phosphorlyated serine or threonine is present.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity.

Methods to calculate sequence identity are known to those of skill in the art and described in further detail below.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

As applied to proteins, the term "substantial identity" means that two protein sequences, when optimally aligned, such as by the programs GAP or BESTFIT using default gap weights, typically share at least about 70 percent sequence identity, alternatively at least about 80, 85, 90, 95 percent sequence identity or more. In certain instances, residue positions that are not identical differ by conservative amino acid substitutions.

The phrases "systemic administration," "administered systemically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

The term "Tctex-1" is an abbreviation for "t-complex-associated-testis-expressed 1" or "T-complex testis-specific protein 1." Both terms are used interchangeably by those of skill in the art to refer to the family of proteins exemplified in FIG. 7. Other terms used by those of skill in the art to refer to human Tctex-1 proteins include "CAG33212", "TCTEL1", "AAB03318" and "CW-1p."

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treating" as used herein is intended to encompass curing as well as ameliorating at least one symptom of any condition or disease.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. Infectious expression vectors, such as recombinant baculoviruses, are used to express proteins in cultured cells. Other infectious expression vectors, such as recombinant adenoviruses and vaccinia viruses, are used as vaccines to express foreign antigens in vacinees. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

B. Novel Tctex-1 Polypeptides and Polynucleotides and Compositions and Methods for Production of the Same The wildtype Tctex-1 polypeptide and polynucleotide sequences encoding such polypeptides from various exemplary species are listed in FIG. 7. The Tctex-1 protein is very well-conserved among both vertebrate and invertebrate species (FIG. 8). For example, the bovine and human Tctex-1 protein sequences are 100% identical, and the rat and murine proteins exhibit about 98% and 93% sequence identity to the human Tctex-1 protein, respectively, and 95% sequence identity with each other. Mammalian Tctex-1 proteins are highly conserved with other vertebrate and even invertebrate Tctex-1 proteins. For example, human Tctex-1 is 78% identical to *Xenopus tropicalis* (frog) Tctex-1 and 72% identical to *Drosophila melanogaster* (fruit fly) Tctex-1.

A consensus protein kinase C (PKC) phosphorylation consensus sequence, [S/T]-x-[R/K], is present in all Tctex-1 proteins, wherein serine (S) or threonine (T) is the actual residue that is phosphorylated, i.e., the phosphorylation site. Most commonly, the consensus sequence is present as TVR (highlighted in FIG. 8), wherein the threonine is phosphorylated (bold in FIG. 8). In the majority of mammalian Tctex-1 proteins, the phosphorylation site is present at position 94. As described in detail in the Examples below, mutating the residue that is phosphorylated in Tctex-1 to a residue which mimics a phosphorylated serine or threonine residue confers upon the mutant Tctex-1 protein the ability to stimulate neurite outgrowth.

Using substantially identical techniques to those described in the Examples below, we have created S82E and S82A Tctex-1 protein mutants which also mimic the phosphorylated Tctex-1 protein. Position 82 (Ser) is part of a predicted CKI (casein kinase I) phosphorylation site, S/T-X(2-3)-S/T-X. Our biochemical data showed that S82E, like the T94E mutant, failed to bind to the dynein intermediate chain (and hence dynein complex). These results thus suggested that S82E mutant protein may share a similar mechanism of action with the T94E mutant protein. Although there has been no obvious biochemical defects of S82A mutant in terms of its ability to bind to dynein, to some surprise, S82A has a severe phenotype in a polarity formation assay in polarized epithelial cells.

A computer-assisted search identified 3 predicted CKI sites in Tctex-1 (at the amino positions-55, 82, and 92), which may also be mutated to mimic the phosphorylations that occur at these sites.

Provided, therefore, are novel Tctex-1 polypeptides which mimic the phosphorylated form of the wildtype Tctex-1 polypeptides and stimulate neurite outgrowth in a cell or subject when the mutants are administered to or expressed in such cell or subject.

In certain embodiments, an isolated, recombinant Tctex-1 polypeptide may comprise a sequence having, for example, at least about 60%, at least about 70%, at least about 80%, at least about 85%, at least about 90%, at least about 95%, at least about 96%, at least about 97%, at least about 98%, or at least about 99% identity to SEQ ID NOs: 1, 3, 5, 7, 9, 11 or 13, wherein the sequence contains a residue that mimics a phosphorylated serine or threonine at a position suitable to confer upon the polypeptide the ability to stimulate neurite outgrowth. In certain embodiments, this residue is present at position 94. In certain embodiments, this residue is present at position 82. In certain embodiments, the residue may be aspartic acid (D), glutamic acid (E), or any other amino acid whose presence at that position confers upon the Tctex-1 protein the ability to stimulate neurite outgrowth and/or neurogenesis. For example, any other amino acid which has chemical properties similar to a phosphorlyated serine or threonine residue, i.e. is negatively charged and/or has a similar geometry or that induces a conformation change in the protein similar to that change a phosphorylated residue would induce, may confer upon the Tctex-1 protein the ability to stimulate neurite outgrowth and/or neurogenesis.

In one embodiment, an isolated recombinant Tctex-1 polypeptide comprises a sequence having at least about 95% identity to SEQ ID NOs: 1, 3, 5, or 7 and E at position 94. In yet other embodiments, an isolated, recombinant Tctex-1 polypeptide comprises a sequence having at least about 95% identity to SEQ ID NOs: 1, 3, 5, or 7 and having any residue at position 94 which confers upon the polypeptide the ability to stimulate neurite outgrowth. Exemplary residues which may be present at position 94 include, but are not limited to, aspartic acid (D), glutamic acid (E), and any other amino acid which has chemical properties similar to a phosphorlyated serine or threonine residue, i.e. it is negatively charged and/or has a similar geometry or that induces a conformation change in the protein similar to that change a phosphorylated residue would induce. In certain embodiments, the isolated, recombinant polypeptide comprises the following sequence (SEQ ID NO: 15): MEDYQAAEETAFVVDEVSNIVKEAIE-SAIGGNAYQHSKVNQWTTNVVEQTLSQLT KLGK-PFKYIVTCVIMQKNGAGLHTASSCF-WDSSTDGSCEVRWENKTMYCIVSAFG LSI.

In another embodiment, an isolated recombinant Tctex-1 polypeptide comprises a sequence having at least about 95% identity to SEQ ID NOs: 1, 3, 5, or 7 and E at position 82. In yet other embodiments, an isolated, recombinant Tctex-1 polypeptide comprises a sequence having at least about 95% identity to SEQ ID NOs: 1, 3, 5, or 7 and having any residue at position 82 which confers upon the polypeptide the ability to stimulate neurite outgrowth. Exemplary residues which may be present at position 82 include, but are not limited to, aspartic acid (D), glutamic acid (E) and any other amino acid which has chemical properties similar to a phosphorlyated serine or threonine residue, i.e. it is negatively charged and/or has a similar geometry. In certain embodiments, the isolated, recombinant polypeptide comprises the following sequence (SEQ ID NO: 16): MEDYQAAEETAFVVDEVSNIV-KEAIESAIGGNAYQHSKVNQWTTNVVEQTLSQLT KLGKPFKYIVTCVIMQKN-GAGLHTASECFWDSSTDGSCTVRWENKT-MYCIVSAFG LSI. In certain embodiments, the isolated, recombinant polypeptide comprises the following sequence (SEQ ID NO: 17): MEDYQAAEETAFVVDEVSNIV-KEAIESAIGGNAYQHSKVNQWTTNVVEQTLSQLT KLGKPFKYIVTCVIMQKN-GAGLHTASACFWDSSTDGSCTVRWENKTMYCIVSAF GLSI.

In certain embodiments, a polypeptide may include an amino acid sequence having at least about 95% identity to the amino acid sequence of the following sequence (SEQ ID NO: 42): MEDYQAAEET AFVVDEVSNI VKEAIESAIG GNAYQHSKVN QWTTNVVEQT LSQLTKLGKP FKYIVTCVIM QKNGAGLHTA SX$_1$CFWDSSTD GSCX$_2$VRWENK TMYCIVSAFG LSI, in which X$_1$ and X$_2$ each represent any amino acid residue. In some embodiments, X$_1$ may represent any amino acid residue except serine. In some embodiments, X$_2$ may represent any amino acid residue except threonine.

Using substantially identical techniques to those described in the Examples below, we have discovered that an isoform or homolog of Tctex-1 proteins, Rp3, which is expressed differently and appears to bind different cargoes from Tctex-1, also has the ability to stimulate neurite outgrowth when phosphorylated. The wildtype Rp3 polypeptide and polynucleotide sequences encoding such polypeptides from various exemplary species are listed in FIG. 9. The Rp3 protein is very well-conserved among both vertebrate and invertebrate species (FIG. 10). For example, the canine and human Rp3 protein sequences are 96% identical, and the rat protein exhibits 90% sequence identity to the human Rp3 protein. Mammalian Rp3 proteins are highly conserved with other vertebrate Rp3 proteins. For example, human Rp3 is 68% identical to Danio rerio (zebrafish) Rp3.

A consensus protein kinase C (PKC) phosphorylation consensus sequence, [S/T]-x-[R/K], is present in all Rp3 proteins, wherein serine (S) or threonine (T) is the actual residue that is phosphorylated, i.e., the phosphorylation site. Most commonly, the consensus sequence is present as TVR (see FIG. 9), wherein the threonine is phosphorylatable (bold in FIG. 9). In the majority of mammalian Rp3 proteins, the phosphorylation site is present at position 95. Mutating the residue that is phosphorylated in Rp3 at position 95 to a residue which mimics a phosphorylated serine or threonine residue is expected to confer upon the mutant Rp3 protein the ability to stimulate neurite outgrowth, substantially as described above and in the Examples for Tctex-1.

The predicted CKI (casein kinase I) phosphorylation site, S/T-X(2-3)-S/T-X is also present at position 83 in the majority of mammalian Rp3 proteins. Accordingly, mutating the residue that is phosphorylated at position 83 in Rp3 to a residue which mimics a phosphorylated serine or threonine residue is expected to confer upon the mutant Rp3 protein the ability to stimulate neurite outgrowth, substantially as described above and in the Examples for Tctex-1.

In one embodiment, an isolated recombinant Rp3 polypeptide comprises a sequence having at least about 95% identity to SEQ ID NOs: 18, 20, 22, 24, 26 or 28 and a residue selected from the group consisting of E at position 95. In yet other embodiments, an isolated, recombinant Tctex-1 polypeptide comprises a sequence having at least about 95% identity to SEQ ID NOs: 18, 20, 22, 24, 26 or 28 and having any residue at position 95 which confers upon the polypeptide the ability to stimulate neurite outgrowth. Exemplary residues which may be present at position 95 include, but are not limited to, aspartic acid (D), glutamic acid (E) and any other amino acid which has chemical properties similar to a phosphorlyated serine or threonine residue, i.e. it is negatively charged and/or has a similar geometry or that induces a conformation change in the protein similar to that change a phosphorylated residue would induce.

In one embodiment, an isolated recombinant Rp3 polypeptide comprises a sequence having at least about 95% identity to SEQ ID NOs: 18, 20, 22, 24, 26 or 28 and a residue selected from the group consisting of E, D, or A at position 83. In yet other embodiments, an isolated, recombinant Tctex-1 polypeptide comprises a sequence having at least about 95% identity to SEQ ID NOs: 18, 20, 22, 24, 26 or 28 and having any residue at position 83 which confers upon the polypeptide the ability to stimulate neurite outgrowth. Exemplary residues which may be present at position 83 include, but are not limited to, aspartic acid (D), glutamic acid (E) and any other amino acid which has chemical properties similar to a phosphorylated serine or threonine residue, i.e. it is negatively charged and/or has a similar geometry or that induces a conformation change in the protein similar to that change a phosphorylated residue would induce.

In certain embodiments, the subject polypeptides may comprise a fusion protein containing at least one domain which increases its solubility and/or facilitates its purification, identification, detection, and/or delivery. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. Linker sequences between a polypeptide of the invention and the fusion domain may be included in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, the subject polypeptides may be modified so that the rate of traversing the cellular membrane is increased. For example, the polypeptide may be fused to a second peptide which promotes "transcytosis," e.g., uptake of the peptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) *Cell* 55:1179-1188). Alternatively, the internalizing peptide may be derived from the *Drosophila antennapedia* protein, or homologs thereof. The 60 amino acid long homeodomain of the homeo-protein antennapedia has been demonstrated to translocate through biological membranes and can facilitate the translocation of heterologous polypeptides to which it is coupled. Thus, polypeptides may be fused to a peptide consisting of about amino acids 42-58 of *Drosophila antennapedia* or shorter fragments for transcytosis (Derossi et al. (1996) *J Biol Chem* 271:18188-18193; Derossi et al. (1994) *J Biol Chem* 269: 10444-10450; and Perez et al. (1992) *J Cell Sci* 102:717-722). The transcytosis polypeptide may also be a non-naturally-occurring membrane-translocating sequence (MTS), such as the peptide sequences disclosed in U.S. Pat. No. 6,248,558.

Transport of therapeutic agents to the brain, spinal cord, and nervous systems is hindered by the presence of the blood-brain barrier (BBB) or blood-nerve barrier (BNB). Accordingly, a subject polypeptide may be modified so that its rate of traversing the BBB is enhanced. For example, polypeptides that bind to endogenous carrier-mediated transport systems could be used to conjugate the subject polypeptides or nucleic acids in such a way that the biological activity of both the drug and the vector are retained. For example, the heavy chain C-fragment of tetanus toxin (TTC) is non-toxic and possesses properties that endow it with the potential to deliver therapeutics to the brain, spinal cord, and peripheral nervous systems. First, TTC is believed to cross the BBB/BNB via activity-dependent internalization and fast retrograde axonal transport from peripheral terminal fields. Second, large proteins fused to TTC are transported efficaciously with their biological activity intact. Fusion protein gene constructs can be engineered in plasmids and transformed into host cells to generate large quantities of fusion protein. Third, due to the combination of a potent and selective affinity of TTC to neuronal membranes, TTC can be delivered systemically to reach all central and peripheral neurons, such as motoneurons, autonomic pre-ganglionics, autonomic post-ganglionics, circumventricular organs (e.g. area postrema), select hypothalamic and brainstem reticular nuclei and primary sensory neurons. Fourth, TTC-protein conjugates can also be transported trans-synaptically to other neurons within nervous system circuits. Fifth, trans-synaptic transfer of TTC is activity-dependent, providing for selective targeting of therapeutic agents to active CNS circuits. Proteins with properties similar to TTC may also be used.

Further, in another embodiment, the polypeptides may be fused with 11 arginine protein transduction domain (Matsushita, M., et al. (2001) *J. Neurosci* 21:6000-6007), which has been shown to delivery polypeptides exclusively into the nuclear compartments of neurons in brain slices. Polypeptide fusions with 11 arginine may optionally comprise a nuclear localization signal.

In another embodiment, truncated polypeptides may be prepared. Truncated polypeptides have from 1 to 20 or more amino acid residues removed from either or both the N- and C-termini. Such truncated polypeptides may prove more amenable to expression, purification or characterization than the full-length polypeptide. In addition, the use of truncated polypeptides may also identify stable and active domains of the full-length polypeptide that may be more amenable to characterization or incorporation into a pharmaceutical composition. Examples of Tctex-1 truncated polypeptides include truncations of the various species and mutants of Tctex-1 disclosed herein that are limited to the first 14 N-terminal amino acids, to the first 54 N-terminal amino acids, to the first 71 N-terminal amino acids, and to the first 92 N-terminal amino acids.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major effect on the biological activity of the resulting molecule. Whether a change in the amino acid sequence of a polypeptide results in a functional homolog may be readily determined by assessing the ability of the variant polypeptide to produce a response similar to that of the wild-type protein.

Polypeptides in which more than one replacement has taken place may readily be tested in the same manner.

Protein homologs may be generated combinatorially. In a representative embodiment of this method, the amino acid sequences for a population of protein homologs are aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential protein sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. A G Walton, Amsterdam: Elsevier pp. 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *PNAS USA* 89:2429-2433; Devlin et al., (1990) *Science* 249: 404-406; Cwirla et al., (1990) *PNAS USA* 87: 6378-6382; as well as U.S. Pat. Nos. 5,223,409, 5,198,346, and 5,096,815).

Alternatively, other forms of mutagenesis may be utilized to generate a combinatorial library. For example, protein homologs may be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137:109-118; Grodberg et al., (1993) *Eur. J. Biochem.* 218:597-601; Nagashima et al., (1993) *J. Biol. Chem.* 268:2888-2892; Lowman et al., (1991) *Biochemistry* 30:10832-10838; and Cunningham et al., (1989) *Science* 244: 1081-1085), by linker scanning mutagenesis (Gustin et al., (1993) *Virology* 193:653-660; Brown et al., (1992) *Mol. Cell Biol.* 12:2644-2652; McKnight et al., (1982) *Science* 232: 316); by saturation mutagenesis (Meyers et al., (1986) *Science* 232:613); by PCR mutagenesis (Leung et al., (1989) *Method Cell Mol Biol* 1:11-19); orby random mutagenesis (Miller et al., (1992) A Short Course in Bacterial Genetics, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying truncated forms of proteins that are bioactive.

Another aspect of the invention relates to polypeptide fragments derived from the full-length polypeptides of the invention. Fragments of the polypeptides may be produced using standard polypeptide synthesis methods as will be known to one of skill in the art. Alternatively, such polypeptide fragments, as well as the subject polypeptides, may be produced using recombinant techniques. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

The present invention also provides isolated nucleic acid sequences that encode all or a substantial portion of the amino acid sequences set forth in SEQ ID NO: 15 or other polypeptides of the invention described above, as well as vectors, host cells, and cultures for the expression and production thereof or for gene therapy methods.

For example, in one embodiment, the polypeptide sequence of SEQ ID NO: 15 may be expressed as a flag-tagged polypeptide (as described in the examples below) using the following sequence (SEQ ID NO: 32): ATGGAA-GACTACCAGGCCGCCGAGGAGACT-GCTTTTGTTGTTGATGAAGTGAG CAACATCG-TAAAAGAGGCCATAGAAAGCGCCATCGGTGGCA ACGCCTATCAG CACAGCAAAGTCAATCAGTGGAC-CACAAACGTAGTGGAGCAGACCTTAAGCC AACT-CACCAAGCTGGGGAAGCCATTTAAGTA-CATCGTGACCTGTGTGATCATG CAGAAGAATGGAGCGGGCCTGCACACG-GCAAGCTCGTGCTTCTGGGACAGCTC CAC-CGATGGGAGCTGCGAAGTGCGATGG-GAGAACAAGACCATGTACTGCATC GTCAGCGCCTTCGGCCTGTCCATCTGA.

For example, in another embodiment, the polypeptide sequence of SEQ ID NO: 16 may be expressed using the following sequence (SEQ ID NO: 33): ATGGAAGACTAC-CAGGCCGCCGAGGAGACTGCTTTTGT-TGTTGATGAAGTGAG CAACATCGTAAAAGAGGC-CATAGAAAGCGCCATCGGTGGCAACGCCTATCAG CACAGCAAAGTCAATCAGTGGACCA-CAAACGTAGTGGAGCAGACCTTAAGCC AACTCAC-CAAGCTGGGGAAGCCATTTAAGTA-CATCGTGACCTGTGTGATCATG CAGAAGAATGGAGCGGGCCTGCACACG-GCAAGCGAATGCTTCTGGGACAGCT CCAC-

CGATGGGAGCTGCACCGTGCGATGG-
GAGAACAAGACCATGTACTGCATC
GTCAGCGCCTTCGGCCTGTCCATCTGA.

For example, in yet another embodiment, the polypeptide sequence of SEQ ID NO: 17 may be expressed using the following sequence (SEQ ID NO: 34): ATGGAAGACTAC-CAGGCCGCCGAGGAGACTGCTTTTGT-TGTTGATGAAGTGAG CAACATCGTAAAAGAGGC-CATAGAAAGCGCCATCGGTGGCAACGCCTATCAG CACAGCAAAGTCAATCAGTGGACCA-CAAACGTAGTGGAGCAGACCTTAAGCC AACTCAC-CAAGCTGGGGAAGCCATTTAAGTA-CATCGTGACCTGTGTGATCATG CAGAAGAATGGAGCGGGCCTGCACACG-GCAAGCGCGTGCTTCTGGGACAGCT CCAC-CGATGGGAGCTGCACCGTGCGATGG-GAGAACAAGACCATGTACTGCATC GTCAGCGCCTTCGGCCTGTCCATCTG.

Isolated nucleic acids which differ from the nucleic acids of the invention due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the polypeptides of the invention will exist. One skilled in the art will appreciate that these variations in one or more nucleotides (from less than 1% up to about 3 or 5% or possibly more of the nucleotides) of the nucleic acids encoding a particular protein of the invention may exist among a given species due to natural allelic variation. Any and all such nucleotide variations and resulting amino acid polymorphisms are within the scope of this invention.

Bias in codon choice within genes in a single species appears related to the level of expression of the protein encoded by that gene. Accordingly, the invention encompasses nucleic acid sequences which have been optimized for improved expression in a host cell by altering the frequency of codon usage in the nucleic acid sequence to approach the frequency of preferred codon usage of the host cell. Due to codon degeneracy, it is possible to optimize the nucleotide sequence without affecting the amino acid sequence of an encoded polypeptide.

Expression vehicles for production of a recombinant polypeptide include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as E. coli. In one aspect of the invention, the subject nucleic acid is provided in a vector comprising a nucleotide sequence encoding a polypeptide of the invention, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a polypeptide. Approaches include insertion of the nucleic acid in viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell. The subject nucleic acids may be used to cause expression and over-expression of polypeptide of interest in cells propagated in culture, e.g. to produce proteins or polypeptides.

This invention also pertains to a host cell transfected with a recombinant gene in order to express a polypeptide of the invention. The host cell may be any prokaryotic or eukaryotic cell. For example, a gene comprising a polypeptide of interest may be expressed in bacterial cells, such as E. coli, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide are known to those in the art.

A cell culture includes host cells, media and other byproducts. Suitable media for cell culture are well known in the art. A polypeptide may be secreted and isolated from a mixture of cells and medium comprising the polypeptide. Alternatively, a polypeptide may be retained cytoplasmically and the cells harvested, lysed and the protein isolated. A polypeptide may be isolated from cell culture medium, host cells, or both using techniques known in the art for purifying proteins, including ion-exchange chromatography, gel filtration chromatography, ultrafiltration, electrophoresis, and affinity purification with antibodies specific for particular epitopes or with the ligand of a fusion tag.

Generally, a nucleic acid encoding a polypeptide of the invention is introduced into a host cell, such as by transfection or infection, and the host cell is cultured under conditions allowing expression of the polypeptide. Methods of introducing nucleic acids into prokaryotic and eukaryotic cells are well known in the art. Suitable media for mammalian and prokaryotic host cell culture are well known in the art. In some instances, the nucleic acid encoding the subject polypeptide is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about OD600 0.45-0.60. The culture is then grown for some more time to give the host cell the time to synthesize the polypeptide. Cultures are then typically frozen and may be stored frozen for some time, prior to isolation and purification of the polypeptide.

Thus, a nucleotide sequence encoding all or part of a polypeptide of the invention may be used to produce a recombinant form of a protein via microbial or eukaryotic cellular processes. Ligating the sequence into a polynucleotide construct, such as an expression vector, and transforming, infecting, or transfecting into hosts, either eukaryotic (yeast, avian, insect or mammalian) or prokaryotic (bacterial cells), are standard procedures. Similar procedures, or modifications thereof, may be employed to prepare recombinant polypeptides by microbial means or tissue-culture technology in accord with the subject invention.

Other embodiments of nucleic acid sequences encoding the polypeptides of the invention, as well as vectors, host cells, and cultures thereof are further described below.

In another embodiment, the nucleic acid encoding a polypeptide of the invention is operably linked to a bacterial promoter, e.g., the anaerobic *E. coli*, NirB promoter or the *E. coli* lipoprotein llp promoter, described, e.g., in Inouye et al. (1985) *Nucl. Acids Res.* 13:3101; *Salmonella* pagC promoter (Miller et al., supra), *Shigella* ent promoter (Schmitt and Payne, *J. Bacteriol.* 173:816 (1991)), the tet promoter on Tn10 (Miller et al., supra), or the ctx promoter of *Vibrio cholera*. Any other promoter can be used in the invention. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

In another embodiment, a signal peptide sequence is added to the construct, such that the polypeptide is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor.

In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp.(Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) *Gene* 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the invention.

In another embodiment, the bacterium further comprises a DNA encoding a second polymerase which is capable of mediating transcription from the second promoter, wherein the DNA encoding the second polymerase is operably linked to a third promoter. In a preferred embodiment, the third promoter is a bacterial promoter. However, more than two different polymerases and promoters could be introduced in a bacterium to obtain high levels of transcription. The use of one or more polymerase for mediating transcription in the bacterium can provide a significant increase in the amount of polypeptide in the bacterium relative to a bacterium in which the DNA is directly under the control of a bacterial promoter. The selection of the system to adopt will vary depending on the specific use of the invention, e.g., on the amount of protein that one desires to produce.

When using a prokaryotic host cell, the host cell may include a plasmid which expresses an internal T7 lysozyme, e.g., expressed from plasmid pLysSL (see Examples). Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., t0 from phage lambda and t4 from the rrnB operon in *E. coli*, to prevent read through transcription and ensure stability of the expressed polypeptide; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in Experimental Manipulation of Gene Expression, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUWI), and pFastBac-derived vectors.

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

In cases where plant expression vectors are used, the expression of a polypeptide may be driven by any of a number of promoters. For example, viral promoters such as the 35S RNA and 19S RNA promoters of CaMV (Brisson et al., 1984, *Nature,* 310:511-514), or the coat protein promoter of TMV (Takamatsu et al., 1987, *EMBO J.*, 6:307-311) may be used; alternatively, plant promoters such as the small subunit of RUBISCO (Coruzzi et al., 1994, *EMBO J.*, 3:1671-1680; Broglie et al., 1984, *Science*, 224:838-843); or heat shock promoters, eg., soybean hsp 17.5-E or hsp 17.3-B (Gurley et al., 1986, *Mol. Cell. Biol.*, 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a polypeptide is an insect system. In one such system, *Autographa californica* nuclear polyhedrosis virus (AcNPV) is used as a vector to express foreign genes. The virus grows in Spodoptera frugiperda cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, *J. Virol.*, 46:584, Smith, U.S. Pat. No. 4,215,051).

In a specific embodiment of an insect system, the DNA encoding the subject polypeptide is cloned into the pBlue-BacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from *Trichoplusia ni* egg cell homogenates; available from Invitrogen, San Diego, Calif.) insect cells, to produce large quantities of appropriately post-translationally modified subject polypeptide. Although it is possible that these cells themselves could be directly useful for drug assays, the subject polypeptides prepared by this method can be used for in vitro assays.

In another embodiment, the subject polypeptides are prepared in transgenic animals, such that in certain embodiments, the polypeptide is secreted, e.g., in the milk of a female animal.

Viral vectors may also be used for efficient in vitro introduction of a nucleic acid into a cell. Infection of cells with a viral vector has the advantage that a large proportion of the targeted cells can receive the nucleic acid. Additionally, polypeptides encoded by genetic material in the viral vector, e.g., by a nucleic acid contained in the viral vector, are expressed efficiently in cells that have taken up viral vector nucleic acid.

Retrovirus vectors and adeno-associated virus vectors are generally understood to be the recombinant gene delivery system of choice for the transfer of exogenous genes in vivo, particularly into mammals. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the antisense E6AP constructs, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150: 4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In choosing retroviral vectors as a gene delivery system for nucleic acids encoding the subject polypeptides, it is important to note that a prerequisite for the successful infection of target cells by most retroviruses, and therefore of stable introduction of the genetic material, is that the target cells must be dividing. In general, this requirement will not be a hindrance to use of retroviral vectors. In fact, such limitation on infection can be beneficial in circumstances wherein the tissue (e.g., nontransformed cells) surrounding the target cells does not undergo extensive cell division and is therefore refractory to infection with retroviral vectors.

Furthermore, it has been shown that it is possible to limit the infection spectrum of retroviruses and consequently of retroviral-based vectors, by modifying the viral packaging proteins on the surface of the viral particle (see, for example, PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) PNAS 86:9079-9083; Julan et al. (1992) *J. Gen Virol* 73:3251-3255; and Goud et al. (1983) *Virology* 163:251-254); or coupling cell surface ligands to the viral env proteins (Neda et al. (1991) *J Biol Chem* 266: 14143-14146). Coupling can be in the form of the chemical cross-linking with a protein or other variety (e.g., lactose to convert the env protein to an asialoglycoprotein), as well as by generating chimeric proteins (e.g., single-chain antibody/env chimeric proteins). This technique, while useful to limit or otherwise direct the infection to certain tissue types, and can also be used to convert an ecotropic vector in to an amphotropic vector.

Moreover, use of retroviral gene delivery can be further enhanced by the use of tissue- or cell-specific transcriptional regulatory sequences which control expression of the genetic material of the retroviral vector.

Another viral gene delivery system utilizes adenovirus-derived vectors. The genome of an adenovirus can be manipulated such that it encodes a gene product of interest, but is inactive in terms of its ability to replicate in a normal lytic viral life cycle (see, for example, Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are well known to those skilled in the art. Recombinant adenoviruses can be advantageous in certain circumstances in that they are capable of infecting non-dividing cells and can be used to infect a wide variety of cell types, including airway epithelium (Rosenfeld et al. (1992) cited supra), endothelial cells (Lemarchand et al. (1992) *Proc. Natl. Acad. Sci. USA* 89:6482-6486), hepatocytes (Herz and Gerard (1993) *Proc. Natl. Acad. Sci. USA* 90:2812-2816) and muscle cells (Quantin et al. (1992) *Proc. Natl. Acad. Sci. USA* 89:2581-2584). Furthermore, the virus particle is relatively stable and amenable to purification and concentration, and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, for example, Jones et al. (1979) Cell 16:683; Berkner et al., supra; and Graham et al. in Methods in Molecular Biology, E. J. Murray, Ed. (Humana, Clifton, N.J., 1991) vol. 7. pp. 109-127). Expression of the inserted genetic material can be under control of, for example, the E1A promoter, the major late promoter (MLP) and associated leader sequences, the E3 promoter, or exogenously added promoter sequences.

Yet another viral vector system useful for delivery of genetic material encoding the subject polypeptides is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97-129). It is also one of the few viruses that may integrate its DNA into non-dividing cells, and exhibits a high frequency of stable integration (see for example Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973). Vectors comprising as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251-3260 can be used to introduce DNA into cells. A variety of nucleic acids have been introduced into different cell types using AAV vectors (see for example Hermonat et al. (1984) *Proc. Natl. Acad. Sci. USA* 81:6466-6470; Tratschin et al. (1985) *Mol. Cell. Biol.* 4:2072-2081; Wondisford et al. (1988) *Mol. Endocrinol.* 2:32-39; Tratschin et al. (1984) *J. Virol.* 51:611-619; and Flotte et al. (1993) *J. Biol. Chem.* 268:3781-3790).

Other viral vector systems may be derived from herpes virus, vaccinia virus, and several RNA viruses.

In addition to viral transfer methods, such as those illustrated above, non-viral methods can also be employed to cause expression of nucleic acids encoding the subject polypeptides, e.g. in a cell in vitro or in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of genetic material by the targeted cell. Exemplary gene delivery systems of this type include liposomal derived systems, polylysine conjugates, and artificial viral envelopes.

In a representative embodiment, genetic material can be entrapped in liposomes bearing positive charges on their surface (e.g., lipofectins) and, optionally, which are tagged with antibodies against cell surface antigens of the target tissue (Mizuno et al. (1992) *No Shinkei Geka* 20:547-551; PCT publication WO91/06309; Japanese patent application 1047381; and European patent publication EP-A-43075). For example, lipofection of papilloma-infected cells can be carried out using liposomes tagged with monoclonal antibodies against PV-associated antigen (see Viac et al. (1978) *J Invest Dermatol* 70:263-266; see also Mizuno et al. (1992) *Neurol. Med. Chir*. 32:873-876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, genetic material encoding the subject chimeric polypeptides can be used to transfect hepatocytic cells in vivo using a soluble polynucleotide carrier comprising an asialoglycoprotein conjugated to a polycation, e.g., polylysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-comprising endosomes (Mulligan et al. (1993) *Science* 260-926; Wagner et al. (1992) *PNAS* 89:7934; and Christiano et al. (1993) *PNAS* 90:2122).

C. Pharmaceutical Compositions Comprising the Novel Tctex-1 Polypeptides and Nucleic Acids and Methods of Use The present invention also provides pharmaceutical compositions comprising a therapeutically effective amount of the polypeptides and nucleic acids described above. In one embodiment, the pharmaceutical composition comprises an isolated, purified recombinant polypeptide. In certain embodiments, the polypeptide is a fusion polypeptide comprising a Tctex-1 polypeptide and a polypeptide that aids in localizing or delivering the Tctex-1 polypeptide. In another embodiment, the pharmaceutical composition comprises an isolated, purified nucleic acid encoding a Tctex-1 polypeptide of the invention. In certain embodiments, the pharmaceutical composition further comprises a pharmaceutically acceptable carrier. Further, the invention provides devices for administering the pharmaceutical compositions, for example, devices for intravenous, intrathecal, intraperitoneal, or subcutaneous injection The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intrathecal, intraperitoneal or subcutaneous), drop infusion preparations or suppositories. For application by the ophthalmic mucous membrane route, compounds of the present invention may be formulated as eyedrops or eye ointments. These formulations may be prepared by conventional means, and, if desired, the compounds may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of agent that may be combined with a carrier material to produce a single dose vary depending upon the subject being treated, and the particular mode of administration.

Methods of preparing these formulations include the step of bringing into association agents of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound thereof as an active ingredient. Compounds of the present invention may also be administered as a bolus, electuary, or paste.

In solid dosage forms for oral administration (capsules, tablets, pills, dragees, powders, granules and the like), the coordination complex thereof is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the compound, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a coordination complex of the present invention with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a supplement or component includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compound.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In another aspect, the present invention provides methods of stimulating neurite outgrowth comprising administering the pharmaceutical composition to a subject. For example, stimulating neurite outgrowth may be used to treat a subject that has a disorder of the nervous system, e.g. by regenerating or repairing damaged nervous system tissue (e.g., the brain, spinal cord, etc.). Accordingly, the present invention provides methods of treating a subject having a nervous system disorder comprising administering a pharmaceutical composition comprising a polypeptide or polynucleotide of the invention to a subject. In certain embodiments, the nervous system disorder is stroke. In other embodiments, the nervous system disorder is spinal cord injury. Such administration may be, for example, intrathecal, peripheral, systemic, or local.

In certain embodiments, the dosage of the subject pharmaceutical compositions will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible effects on the timing of administration of the formulation, may need to be identified for any particular compound of the present invention. This may be accomplished by routine experiment as described herein, using one or more groups of animals (preferably at least 5 animals per group), or in human trials if appropriate. The effectiveness of any compound and method of treatment or prevention may be assessed by administering the supplement and assessing the effect of the administration by measuring one or more indices associated with the neoplasm of interest, and comparing the post-treatment values of these indices to the values of the same indices prior to treatment.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the LD50 and the ED50. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the ED50 with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

D. Combination Therapies

The Tctex-1 polypeptides and compositions thereof described herein can be used in combination with other therapies to promote neuron growth. A wide variety of nervous system disorders can be treated using such combinations; examples include stroke, spinal cord injury, trauma, and degenerative disorders. The Tctex-1 polypeptides and compositions thereof described herein can promote neurite outgrowth, and a second therapy can stimulate the growing neurons to grow to the appropriate places, form synapses, etc., to restore lost function. Neurite outgrowth can thus be given direction and specificity under the influence of instructive signals from a targeted therapy. The therapies being combined can be administered simultaneously or serially. Three or more therapies may be combined.

Tctex-1 polypeptide treatment, for example, can be combined with physical therapy, by which a subject receives training to perform a particular motion. The physical therapy causes stimulation of particular neurons and can thereby strengthen and reinforce synapses formed by outgrowing neurons. The physical therapy can be administered by a human therapist, by continuous passive motion machines, or by robots. In particular, the objective and repeatable therapy provided by haptic robots such as those described in U.S. Pat. No. 5,466,213 to Hogan et al., hereby incorporated herein by reference, or U.S. Application Publication No. US 2006/0106326-A1 to Krebs et al., hereby incorporated herein by reference, can potentiate the recovery stimulated by Tctex-1 polypeptide treatment.

A subject recovering, for example, from stroke, spinal cord injury, or other nervous system disorder can undergo a rigorous regimen of physical therapy in an attempt to relearn motions lost as a result of the stroke or other injury. The relearning process involves stimulating existing neurons to modulate existing synapses or form new synapses so that those neurons can effectuate the motions being relearned. The relearning process may also involve neuron regeneration, but this process is greatly inhibited in the central nervous system by a variety of mechanisms. Therapy with Tctex-1 polypeptides can help overcome CNS regeneration inhibition and allow CNS neurons to participate in the recovery process.

Other forms of therapy that may be combined with Tctex-1 polypeptide therapy include electrical stimulation of portions of the nervous system (such as in deep brain stimulation), and drug therapy, as follows.

Drugs typically used to treat Alzheimer's disease or related symptoms include cholinesterase inhibitors (such as tacrine and donepezil), rivastigmine, galantamine, galanthamine, memantine, metrifonate, bryostain, methylxanthine, non-steroidal anti-inflammatory drugs (rofecoxib, naxopren, celecoxib, aspirin, ibuprofen), vitamin E, selegiline, estrogen, ginkgo biloba extract, antidepressants, neuroleptics and mood stabilizers.

Drugs typically used to treat pain include analgesics (acetaminophen, acetaminophen with codeine, hydrocodone with acetaminophen, morphine sulfate, oxycodone, oxycodone with acetaminophen, propoxyphene hydrochloride, propoxyphene with acetaminophen, tramadol, tramadol with acetaminophen) and non-steroidal anti-inflammatory drugs (NSAIDs; diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen, naproxen sodium, oxaprozin, piroxicam, sulindac, tolmetin sodium, choline and magnesium salicylates, choline salicylate, magnesium salicylate, salsalate, sodium salicylate).

Drugs typically used to treat ALS or related symptoms include riluzole, baclofen, tiranadine, dantrolene, benzodiazepines (such as diazepem), gabapentin, NSAIDs, cox2 inhibitors, tramadol, antidepressants, selective serotonin re-uptake inhibitors, selective dopamine blockers, branch-chain amino acids, phenytoin, quinine, lorazepam, morpine, arimoclomol, and chlorpromazine.

Drugs typically used to treat Parkinson's disease or related symptoms include levodopa, carbidopa, selegiline, bromocriptine, pergolide, amantadine, trihexphenidyl, benztropine, COMT inhibitors (catechol-O-methyl transferase), anticholinergics, dopamine precursors, dopamine receptor agonists, MAO-B inhibitors, and peripheral decarboxylase inhibitors.

Drugs typically used to treat Huntington's disease or related symptoms include neuroleptic agents, dopamine receptor blockers (such as haloperidol and perphenazine), presynaptic dopamine depletors (such as reserpine), clozapine, antidepressants, mood stabilizer, and antipsychotic agents.

Drugs typically used to treat multiple sclerosis or related symptoms include interferon beta-1a, interferon beta-1b, glatiramer, mitoxantrone, natalizumab, corticosteroids (such as prednisone, methylprednisolone, prednisolone, dexamethasone, adreno-corticotrophic hormone (ATCH), and corticotropin), chemotherapeutic agents (such as azathiprine, cyclophosphamide, cyclosporin, methotrexate, cladribine), amantadine, baclofen, meclizine, carbamazepine, gabapentin, topiramate, zonisamide, phenytoin, desipramine, amitriptyline, imipramine, doxepin, protriptyline, pentoxifylline, ibprofen, aspirin, acetaminophen, hydroxyzine, antidepressants, and antibodies that bind to α4-integrin (b1 and b7), e.g., TYSABRI® (natalizumab).

Compounds typically used to treat chronic stroke include benzodiazepines (such as midazolam), amphetamines (such as dextroamphetamine), type IV phosphodiesterase inhibitors (such as rolipram), type V phosphodiesterase inhibitors (such as sildenafil), and HMG-coenzyme A reductase inhibitors (such as atorvastatin and simvastatin) and nitric oxide donors, especially indirect nitric oxide donors. Other drugs of interest in treating stroke include inhibitors of mitochondrial permeability transition such as heterocyclics (methiothepin, mefloquine, propiomazine, quinacrine, ethopropazine, cyclobenzaprine, propantheline), antipsychotics (trifluoperazine, triflupromazine, chlorprothixene, promazine, thioridazine, chlorpromazine, prochlorperazine, perphenazine, periciazine, clozapine, thiothixene, pirenzepine), antidepressants (clomipramine, nortriptyline, desipramine, amitriptyline, amoxepine, maprotiline, mianserin, imipramine, doxepin), and antihistamines (promethazine, flufenazine, pimethixine, loratadine), mitochondial uncouplers such as 2,4-dinitrophenol, and antineoplastic drugs such as DNA intercalators (mithramycin).

Drugs typically used to treat acute stroke and spinal cord injury include thrombolytics (tissue plasminogen activator, alteplase, tenecteplase, and urokinase), antiplatelet agents (aspirin, clopidogrel, abciximab, anagrelide, dipyridamole, eptifibatide, ticlodipine, tirofiban), and anticoagulants (warfarin, heparin).

Drugs typically used to treat arthritis include cox2 inhibitors (etoricoxib, valdecoxib, celecoxib, rofecoxib), NSAIDs, and analgesics.

The drugs described above can be combined with one another and with other substances. Combination therapies include conjoint administration with nicotinamide, NAD+ or salts thereof, other Vitamin B3 analogs, and nicotinamide riboside or analogs thereof. Carnitines, such as L-carnitine, may be co-administered, particularly for treating cerebral stroke, loss of memory, pre-senile dementia, Alzheimer's disease or preventing or treating disorders elicited by the use of neurotoxic drugs. Cyclooxygenase inhibitors, e.g., a COX-2 inhibitor, may also be co-administered for treating certain conditions described herein, such as an inflammatory condition or a neurologic disease.

A combination drug regimen may also include other agents or compounds for the treatment or prevention of neurodegenerative disorders, including stroke, Alzheimer's disease, ALS, Parkinson's disease, Huntington's disease, multiple sclerosis or secondary conditions associated with any of these conditions.

E. Kits

The present invention provides kits for treating disorders of the nervous system in a subject. For example, a kit may also comprise one or more polypeptides or nucleic acids of the present invention, or a pharmaceutical composition thereof. Kit components may be packaged for either manual or partially or wholly automated practice of the foregoing methods. In other embodiments involving kits, this invention contemplates a kit including compositions of the present invention, and optionally instructions for their use. In other embodiments, a kit may further comprise controls, reagents, buffers, and/or instructions for use. Such kits may have a variety of uses, including, for example, imaging, diagnosis, therapy, and other applications.

EXAMPLES

The invention, having been generally described, may be more readily understood by reference to the following examples, which are included merely for purposes of illustration of certain aspects and embodiments of the present invention, and are not intended to limit the invention in any way.

EXAMPLE 1

Tctex-1 is Enriched in Growing Axons of Cultured Hippocampal Neurons

Within the first 24 h after plating, cultured hippocampal neurons develop several relatively symmetric minor processes 20-30 $\mu m_{ave}$ in length (stage 2 cells); Tctex-1 was evenly distributed throughout the cell body and minor neurites during this stage (data not shown). However, during development through stages 2-3, Tctex-1 immunoreactivity increased considerably in the longest neurites that had large growth cones and abundant microtubules (FIGS. 1A-C), morphological characteristics of nascent axons. Quantification of Tctex-1 labeling intensity relative to that of tubulin confirmed the Tctex-1 signal had a gradient in nascent axons: low at the proximal end and high at the distal region (FIG. 1H). By contrast, very little Tctex-1 signal was detected in the growth cones of minor neurites. At the axonal growth cone, Tctex-1 co-localized with tyrosinated (tyr)-tubulin in the central region (FIGS. 1A, B). However, Tctex-1-labeled puncta were also arrayed on F-actin microfilaments that extended into the peripheral lamellipodial veil (FIGS. 1D, E).

Upon reaching stage 3, Tctex-1's distribution appeared to be even more polarized, as it became considerably enriched in the distal axonal shaft and its growth cone (FIGS. 1F, G). In contrast to Tctex-1, immunolabeling for DHC (dynein heavy chain), DIC (dynein intermediate chain), or dynactin subunit $p_{150}^{glued}$ (data not shown) did not reveal any particular enrichment within axons or growth cones. Furthermore, little or no labeling for dynein light chain rp3, a Tctex-1 homologue was found in young neuronal cultures (data not shown).

Tight control of the asymmetric and dynamic localization of Tctex-1 during neuronal development appears to be a key element providing forces that shape the neuron. For example, high-level Tctex-1 accumulation in the distal region and growth cones of a given neuron at stage 2-3 empowers that neurite to elicit the fastest growth rate and hence become "committed" to the axonal fate. Conversely, the near absence of Tctex-1 in minor neurites could prevent their growth. However, what happens to the axon happens later in the minor neurites. Tctex-1 reappears in the minor neurites at stage 4, hence, allowing dendritic extension and branching. The ability of Tctex-1 to affect dendrite development was consistent with Tctex-1 immunoreactivity being readily detected in dendritic shafts in 3 DIV (days in vitro) cultures, even though Tctex-1 is low in minor neurites of young cultured neurons. The importance of Tctex-1 in neurite development is well correlated with its abundance in fetal brains (Kai, N., et al. (1997). *J Neurosci Res* 48, 407-424) and postmitotic young neurons in adult brain (Chuang, J. Z., et al. (2001) *J Neurosci* 21, 5501-5512).

EXAMPLE 2

Tctex-1 Mediates Neuritogenesis

An antisense (AS) oligonucleotide against Tctex-1 was used to carry out loss-of-function experiments to study its role during hippocampal neuronal development. The reduction of Tctex-1 protein, but not control proteins (e.g., DHC, tubulin), was confirmed by immunoblotting (FIG. 2E) and quantitative immunofluorescence (data not shown). Almost all cells treated with no oligonucleotide (data not shown) or with a scrambled control oligonucleotide (FIGS. 2A, D) were able to reach stage 2 or stage 3 of neuritic development after 24-36 h; in contrast, the majority of Tctex-1-AS treated cells failed to develop neurites (FIGS. 2A, D). The Tctex-1 suppressed neurons had segmented lamellipodia, but neither typical neurites nor growth cones. Some Tctex-1 suppressed neurons displayed short thin tubulin$^+$ processes that penetrated the lamellipodial veil (FIGS. 2B, C). Morphometric analysis revealed that although more than 80% of 36 h control neurons reached stage 3, less than 2% of AS treated cells reached this stage (FIG. 2D).

Similar results were also obtained by examining neurons with Tctex-1 suppressed by RNA interference. Neurons transfected with Tctex-1-siRNA oligonucleotides, identified by lower levels of Tctex-1 immunolabeling, were almost always associated with cells arrested at stage 1 of neuritic development (data not shown).

In order to unambiguously identify neurons targeted with Tctex-1-siRNA, we generated a plasmid harboring both the Tctex-1 hairpin siRNA and the GFP cDNA (i.e., Tctex-1-siRNA/GFP). The silencing effect of this plasmid was confirmed in both transfected HEK cells (data not shown) and in transfected neurons (FIG. 2F). When neurons were transfected with Tctex-1-siRNA/GFP plasmid 2 h after plating and examined 20-22 h later, almost all GFP$^+$ neurons had specific reduction of Tctex-1 immunofluorescence, but not tubulin immunofluorescence (FIGS. 2G-J, arrows). Again, the majority of the GFP$^+$, siRNA targeted cells failed to develop neurites and arrested at stage 1. These siRNA targeted cells are neurons because they were labeled by TuJ1 antibody, which recognizes the neuron-specific β-III tubulin. By contrast, control neurons transfected with scrambled control-siRNA/GFP plasmid developed neurites normally (data not shown). These results consistently suggested that proper Tctex-1 dosage is essential for the initial events of neurite development, such as neurite sprouting from the spherical cell bodies.

To examine Tctex-1's role in neurite extension, neurons were treated with either Tctex-1-AS or Tctex-1-siRNA/GFP~15 h after plating and analyzed 20 h later. While most of control cells reached stage 3, the majority of Tctex-1 suppressed cells were arrested at stage 2 (FIGS. 2K-N). These results clearly suggested that Tctex-1 suppression could effectively inhibit neurite extension and, hence suppress differentiation during stage 2-3 development.

EXAMPLE 3

Ectopic Tctex-1 Expression Promotes Neurite Outgrowth and Abolishes Neuronal Polarity Gain-of-function studies were subsequently performed to examine the phenotypes of neurons overexpressing Tctex-1. For controls, dissociated neurons were singly transfected with GFP, GFP-DIC, or Flag-DIC (data not shown) or co-transfected with Flag-DIC and GFP (FIGS. 3L-O). The kinetics of neurite development, and the morphological parameters of all control neurons were undistinguishable from those of non-transfected neurons. The cells exhibited normal development through stage 2 (FIGS. 3D-I) and stage 3, at which time they developed a single Tau1$^+$ axon and several much shorter minor neurites (FIG. 3L).

By contrast, almost all Flag-Tctex-1 transfected neurons displayed multiple abnormally long Tau1$^+$ axon-like neurites (FIGS. 3A-C). These Tau1$^+$ neurites were also positive for several other axonal markers including APC, Cdc42, synapsin 1, and synaptotagmin (data not shown) (Zhou, F. Q., et al. (2004) *Neuron* 42, 897-912; Fletcher, T. L., et al. (1991) *J Neurosci* 11, 1617-1626; Schwambom, J. C., and Puschel, A. W. (2004) *Nat Neurosci* 7, 923-929). Statistical analysis confirmed that the axon numbers (FIG. 3L) and the lengths (FIG. 3N) were significantly higher in Flag-Tctex-1 transfected cells than in Flag-DIC transfected control cells (data not shown). Despite the increased numbers of axons, the total number of primary neurites extended from Tctex-1 transfected cells was not significantly different from that of control cells (FIG. 3M). Taken together, these results suggest that the ability of Tctex-1 to enhance neurite outgrowth is rather specific, and ectopic expression of other dynein subunit such as DIC cannot imitate the axogenic effects mediated by Tctex-1. Furthermore, Tctex-1 overexpression enhanced neurite extension, rather than increased neurite sprouting.

Live neurons transfected with GFP (data not shown) or GFP together with Flag-Tctex-1 (FIGS. 3J, K), were also observed by time-lapse video microscopy and sequential photography. In these experiments, neurite development could be traced in the same cells over a period of time, and our results confirmed the accelerated rate of neurite outgrowth in Tctex-1 expressing neurons.

We then sought to determine whether Tctex-1's ability to promote neurite outgrowth remains throughout neuronal differentiation. For this purpose, neurons at 3 DIV were transfected with Tctex-1 or GFP and harvested 18 h later. Flag-Tctex-1 expressing neurons displayed significantly longer axons (Tau1$^+$/MAP2$^-$ neurites) than those of GFP-transfected cells (FIGS. 4A, B). The mean length of axons (2,113±219 μm) of Tctex-1 transfected neurons was almost 3-fold longer than in GFP transfected cells (720+38 μm;

Table 1). In addition, the 4 DIV Tctex-1 transfected neurons bore more than $2.5_{ave}$ axons compared to the control neurons with $1.2_{ave}$ axons (Table 1).

Tctex-1 transfected neurons also had significantly longer and more elaborated MAP2+ dendrites relative to the control neurons (FIGS. 4C-L). Quantitative morphometric analysis showed that Tctex-1 and GFP transfected neurons had 18.6±2.2 vs. 8.4±1.8 branches per dendrite, respectively.

Both the axogenic and dendritogenic effect elicited by Tctex-1 appeared to be dosage-dependent: neurons transfected with a smaller amount of Tctex-1-expressing plasmid exhibited a less prominent, albeit still statistically significant, effect (Table 1).

TABLE 1

| Overexpressed protein | Number Axons | Mean Axonal Length | Number Dendritic Branches | Mean Dendritic Length |
|---|---|---|---|---|
| GFP | 1.24 ± 0.2 | 720 ± 38 | 8.4 ± 1.8 | 238 ± 24 |
| Tctex-1-WT (2 µg) | 2.45 ± 0.3* | 2113 ± 219* | 18.6 ± 2.2* | 604 ± 18* |
| Tctex-1-WT (1 µg) | 1.85 ± 0.2* | 1228 ± 46* | 14.2 ± 2.4* | 378 ± 28* |
| T94E | 2.21 ± 0.2* | 1915 ± 147* | 16.8 ± 1.6* | 524 ± 34* |
| T94A | 1.38 ± 0.2 | 840 ± 26 | 9.2 ± 1.2 | 256 ± 16 |
| CA-Rho | 1.08 ± 0.2 | 240 ± 16* | 4.2 ± 0.8* | 80 ± 12* |
| DN-Rac | 1.20 ± 0.2 | 298 ± 24* | 2.4 ± 0.8* | 40 ± 10* |
| Tctex-1 + CA-Rho | 1.20 ± 0.2 | 585 ± 84 | 6.2 ± 0.6 | 220 ± 46 |
| Tctex-1 + DN-Rac | 1.1 ± 0.2 | 510 ± 68 | 2.2 ± 0.2* | 68 ± 10* |

Tctex-1 expression may promote neuritogenesis by overcoming suppression by myelin-associated glycoprotein.

EXAMPLE 4

Tctex-1 Mediated Neurite Growth is Dynein-Independent

To explore the mechanism underlying Tctex-1 mediated neuritic development, we first asked whether the inhibitory effect caused by Tctex-1 knockdown was related to impaired cargo binding for dynein transport. Our first approach to test this possibility was asking whether interference with general dynein activity by overexpression of dynactin subunit p50 dynamitin (Echeverri, C. J., et al. (1996). *J Cell Biol* 132, 617-633) would produce a similar phenotype to that caused by loss of Tctex-1. Consistent with the notion that the centrosomal Golgi localization required dynein motor activity (Corthesy-Theulaz, I., et al. (1992). *J Cell Biol* 118, 1333-1345), neurons overexpressing myc-p50 had a dispersed Golgi apparatus (data not shown). Despite that, and unlike Tctex-1 suppressed neurons, neurons transfected with p50 were capable of extending minor neurites and developing an axon (data not shown), even though alterations in neuritic caliber including swellings and a slight reduction of axonal length were commonly detected (data not shown).

To directly test the role of dynein motor activity in neuron development, we performed morphometric analyses on neurons co-transfected with DHC-siRNA and GFP plasmid. The gene silencing and function blocking effects of this DHC-siRNA plasmid has been demonstrated by (Shu, T., et al. (2004) *Neuron* 44, 263-277) and confirmed by us (data not shown). As shown in FIGS. 5A-F, 1 DIV neurons targeted with DHC-siRNA developed rather normally through stages 2 and 3, by which time a single axon was extended. Taken together, these results suggested that dynein motor activity was not critically required for the initial elaboration of neurites and/or axon specification. These results further indicated that neither the inhibitory effect of Tctex-1 silencing nor the axogenic effect of Tctex-1 overexpression is likely to be due to its dynein-related role.

Previous biochemical evidence revealed that a pool of Tctex-1 exists that is not associated with dynein complex (Tai, A. W., et al. (1998) *J Biol Chem* 273, 19639-19649). To date, the cellular function of the complex-free Tctex-1 and the regulation of Tctex-1 assembly into dynein complex are unknown. To gain insight into whether the "complex" or the "free" form of Tctex-1 is involved in neurite development, we attempted to identify a Tctex-1 mutant unable to incorporate into the dynein complex and examine its effect on neurite outgrowth and axonal polarity in transfected neurons. Tctex-1 is assembled into dynein complex through its interaction with DIC (Mok, Y. K., et al. (2001) *J Biol Chem* 276, 14067-14074; Tai, A. W., et al. (2001) *J Cell Biol* 153, 1499-1509). The DIC binding region of Tctex-1 has been mapped to the region between amino acids 55 and 95 (Mok et al., 2001). In this region, we detected a consensus protein kinase C (PKC) phosphorylation site at threonine 94 (T94). Because purified Tctex-1 can be phosphorylated by PKC in an in vitro assay (our unpublished results), we reasoned that it was probable that the phosphorylation at T94 serves as a mechanism regulating its interaction with DIC. Site-directed Tctex-1 mutants of the wildtype sequence deposited as NP_777045 with NCBI (SEQ ID NO: 1 in FIG. 7) having the T94 replaced with alanine (T94A) (polypeptide sequence SEQ ID NO: 35: MEDYQAAEETAFVVDEVSNIVKEAIE-SAIGGNAYQHSKVNQWTTNVVEQTLSQLT KLGK-PFKYIVTCVIMQKNGAGLHTASSCF-WDSSTDGSCAVRWENKTMYCIVSAF GLSI; polynucleotide sequence encoding flag-tagged polypeptide sequence SEQ ID NO: 36: ATGGAAGACTACCAGGC-CGCCGAGGAGACTGCTTTTGTTGTTGAT-GAAGTGAG CAACATCGTAAAAGAGGCCATA-GAAAGCGCCATCGGTGGCAACGCCTATCAG CACAGCAAAGTCAATCAGTGGACCA-CAAACGTAGTGGAGCAGACCTTAAGCC AACTCAC-CAAGCTGGGGAAGCCATTTAAGTA-CATCGTGACCTGTGTGATCATG CAGAAGAATGGAGCGGGCCTGCACACG-GCAAGCTCGTGCTTCTGGGACAGCTC CAC-CGATGGGAGCTGCGCCGTGCGATGG-GAGAACAAGACCATGTACTGCATC GTCAGCGCCTTCGGCCTGTCCATCTGA) or glutamic acid (T94E) (see SEQ ID NOs: 15 and 32 above for polypeptide sequence and nucleic acid sequence encoding the flag-tagged polypeptide) were generated to mimic the unphosphorylated and the phosphorylated Tctex-1, respectively, and these mutants were then tested for their ability to bind endogenous DIC and dynein complex in transiently transfected 293T cells. Both Flag-wild type (WT) Tctex-1 and Flag-T94A, but not Flag-T94E, were co-immunoprecipitated with endogenous DIC using anti-DIC antibody (FIG. 5G). Converse experiments consistently showed that anti-Flag Ab co-precipitated DIC from cells co-expressing either Flag-WT or Flag-T94A, but not Flag-T94E (data not shown). The inability of T94E binding to DIC in these experiments predicted that T94E was not able to be incorporated into dynein complex.

The organization of the ectopically expressed Tctex-1 related to the dynein complex was also examined by velocity density gradient sedimentation. Gradient fractions of cell lysates containing transfected Flag-tagged, WT, T94E, or T94A were immunoblotted for p150$^{Glued}$, DIC, and Flag. As shown in FIG. 5I, in all cases, both markers for dynein complexes (e.g., DIC) and dynactin complexes (e.g., p150$^{Glued}$) were sedimented at 19-20S, suggesting that overexpression of Tctex-1 and its mutants did not perturb the integrity of dynein complexes. Moreover, both Flag-WT and T94A co-sedimented with the dynein/dynactin complexes at 19-20S (FIG. 5I); immunoprecipitation of these dynein-containing fractions with anti-DIC antibody co-precipitated both endogenous as well as the transfected Flag-WT or Flag-T94A (FIG. 5H). These results suggested that the ectopically expressed Flag-WT partially replaced the endogenous Tctex-1 and incorporated into the dynein complex, even though, as predicted, a fraction of Flag-WT and Flag-T94A were detected outside the dynein complexes and distributed on the top of the gradient (fractions 9-12; FIG. 5I).

2). In fact, the phalloidin staining of Tctex-1-transfected cells closely resembles that of cytochalasin D-treated neurons, which had no F-actin enrichment at the axonal tip. Moreover, while the tubulin level was normally tapered off at the very distal end of control cells, the tubulin levels were relative constant throughout the distal ends of axons in both Tctex-1-transfected and cytochalasin D-treated cells. Intriguingly, previous report showed that various treatments that disassemble actin also induce multiple axon-like processes on cultured hippocampal neurons (Bradke, F., and Dotti, C. G. (1999) *Science* 283, 1931-1934). The common phenotypes shared by Tctex-1-transfected and cytochalasin D-treated neurons prompted us to speculate that Tctex-1 may regulate axonal outgrowth by attenuating the stability of actin microfilaments.

TABLE 2

|  | 35 μm | 30 μm | 25 μm | 20 μm | 15 μm | 10 μm | 5 μm |
|---|---|---|---|---|---|---|---|
| Tubulin (Control) | 140 ± 15 | 138 ± 12 | 120 ± 12 | 90 ± 16 | 60 ± 10 | 40 ± 12 | 20 ± 4 |
| Tubulin (Tctex) | 145 ± 16 | 140 ± 18 | 136 ± 14 | 128 ± 12 | 130 ± 6 | 110 ± 8 | 90 ± 6 |
| Actin (Control) | 30 ± 6 | 35 ± 8 | 30 ± 6 | 34 ± 10 | 60 ± 8 | 135 ± 16 | 215 ± 22 |
| Actin (Tctex) | 30 ± 4 | 35 ± 6 | 30 ± 2 | 22 ± 4 | 26 ± 4 | 32 ± 8 | 40 ± 6 |
| Tubulin (CytoD) | 140 ± 12 | 140 ± 14 | 130 ± 12 | 140 ± 12 | 120 ± 8 | 110 ± 14 | 110 ± 6 |
| Actin (CytoD) | 20 ± 5 | 15 ± 5 | 20 ± 4 | 10 ± 2 | 10 ± 2 | 10 ± 2 | 20 ± 4 |

In contrast, Flag-T94E was absent from the dynein-containing 19-20S fractions but exclusively detected in the light fractions of the gradient. Consistently, only endogenous Tctex-1, but not Flag-T94E, was detected in the DIC immunoprecipitates of the 19-20S, dynein-complex (FIG. 5H). These results collectively demonstrated that phosphorylation at T94 may be a mechanism to dissociate Tctex-1 from dynein complexes and thus, the T94E mutant was only found in the fractions outside the dynein complex pool.

We then examined how overexpression of the T94E and T94A mutant affects neurite extension. Like WT Tctex-1 transfected neurons, 4 DIV neurons ectopically expressing T94E for 18 h displayed multiple axon-like processes (FIG. 5J). Other morphological features induced by T94E were also indistinguishable from neurons transfected with WT Tctex-1. Namely, the axons and dendrites were significantly longer, and the dendrites had more branches compared to those of GFP-transfected control neurons (Table 1). In striking contrast, T94A mutant overexpression did not induce the axogenic/dendritogenic phenotype caused by WT and T94E mutant overexpression (FIG. 5K). Together, these results argued that the T94 phospho-mimic, complex-free form of Tctex-1 was likely to be an activeform of Tctex-1 for the enhanced neurite outgrowth activity. These results provided additional support that the neuronal phenotype caused by Tctex-1 occurs through a dynein-independent pathway.

EXAMPLE 5

Tctex-1 Modulates the Actin Cytoskeleton Through a RhoGTPase-Dependent Pathway

During the course of the above-described experiments, it became obvious to us that Tctex-1 transfected neurons had consistently less F-actin labeling than control nontransfected neurons, or those transfected with control proteins such as GFP-DIC (FIGS. 3C vs. 3F), or Flag-DIC (FIG. 6B). The loss of the F-actin signal was particularly prominent in neurite tips. Quantification of phalloidin labeled F-actin confirmed these observations (FIG. 6A; identical data presented in Table 2).

It is now well established that RhoGTPase family proteins play pivotal roles in regulating actin cytoskeleton organization (Ridley, A. J., et al. (1992) *Cell* 70, 401-410). Rho and Rac have opposing effects on actin organization, and differentially affect neurite outgrowth and axon formation. For example, neurite outgrowth is promoted by Rac 1 and inhibited by RhoA. To test whether Tctex-1-induced neurite outgrowth and axonal formation involve a modulation of actin assembly through a RhoGTPase-dependent pathway, we asked if the constitutively active (CA) form of RhoA (G14V) or the dominant negative (DN) form of Rac1 (T17N) could reverse Tctex-1-mediated phenotypes in cultured neurons.

Neurons singly transfected with either HA tagged CA-RhoA (FIGS. 6D, E) or DN-Rac1 (FIGS. 6F, G) mutants displayed a dramatic inhibition of axon extension and formation of MAP2$^+$ dendrites (also see Table 1). However, neurons co-expressing CA-RhoA together with Tctex-1 had a single axon with an average length intermediate between those of neurons singly transfected with CA-RhoA or Tctex-1 (FIGS. 6H, I; Table 1). Similarly, Tctex-1 overexpression partially reversed the inhibition of axon elongation induced by co-expression of DN-Rac1, even though these neurons still failed to elaborate MAP2$^+$ dendrite processes (FIGS. 6J, K). Collectively, these results suggested that Tctex-1-induced phenotypes in neurons mimic Rac I activation or RhoA inactivation, or both.

Tctex-1 overexpression in fibroblasts yielded morphological changes—enhanced membrane ruffle and loss of stress fibers (data not shown)—reminiscent of those induced by the active form of Rac1. A pull-down assay revealed that Tctex-1 overexpression in 3T3 cells induced a ~2-fold increase in Rac1 activity, but not RhoA activity (data not shown), without affecting total Rac1 levels (FIG. 6C). Furthermore, converse experiments showed that neurons transfected with Tctex-1-siRNA/GFP had significantly lower Rac1 activity compared to the control-siRNA/GFP transfected cells (FIG. 6C). These biochemical results consistently suggested that Tctex-1 upregulated Rac1 activity.

To further test the possibility that Tctex-1 could regulate the actin cytoskeleton through Rac1 activation, we asked whether CA-Rac1 overexpression could compensate for the Tctex-1-siRNA-mediated inhibitory effect on neurite development. To this end, we first showed that neurons transfected with myc-CA-Rac1 alone induced dosage-dependent phenotypic changes. Cells transfected with a lower amount (1 μg) of CA-Rac1 extended a single long axon and several short minor processes, with growth cones that display prominent lamellipodial veils (FIG. 6L). Higher doses of CA-Rac1, mimicking Tctex-1 overexpression, also induced multiple axon-like neurites (2 μg in FIG. 6M, 4 μg in FIG. 6N). Many of these axon-like neurites exhibited excess lamellipodial "waves", similar to those described in neurons overexpressing Rac-GEF (guanine nucleotide exchange factor)-Tiam1 (T-cell lymphoma invasion and metastasis protein) Kunda, P., et al. (2001) *J Neurosci* 21, 2361-2372. These structures were not detected in Tctex-1-overexpressing neurons.

As shown in FIGS. 6O-Q, neurons co-transfected with equal amounts of Tctex-1-siRNA/GFP and myc-Rac1-CA plasmids (2 μg each) displayed a single axon with several minor neuritis. These results suggested that Rac1 is able to overcome the neuritic inhibitory effected exerted by Tctex-1-siRNA. The minor neurites in these double transfected cells displayed "veiled" growth cones, closely resembling neurons with lower-level Rac1 overexpression (FIG. 6L). These results, together with the preceding results, collectively suggested that the neurite and axon development induced by Tctex-1 was likely to be mediated through Rac1-mediated pathway(s).

EXAMPLE 6

Experimental Methods for Studies of the Expression and Function of Tctex-1 Described in Examples 1-5

Antisense RNA, siRNA Oligonucleotide, Antibody, Plasmid Construct, and Virus Production Phosphorothioate (*)-modified antisense oligos (rat Tctex-1 (SEQ ID NO: 37: 5'-TGCTCACTTCATCCACA*A*C*; control oligo (SEQ ID NO: 43: 5'-TGTCACTTCTCACACC*A*A*) were purchased from BioSource (Camarillo, Calif.). Tctex-1 siRNA oligonucleotides (SEQ ID NO: 38: GUCAACCAGUGGAC-CACUAdTdT; SEQ ID NO: 44: UAGUGGUCCACUGG-UUGACdTdT) were purchased from Qiagen-Xeragon (Germantown, Md.). The Tctex-1-siRNA plasmid was constructed in a pBS/U6 vector using 5'-GGTTACACACCG-CAAGTTCCCCATGGGGAACTTGCGGTGT-GTAACCCTTTTTA (SEQ ID NO: 39) and 5'-AGCT-TAAAAAGGGTTACACACCGCAAGTTCCCCATGGG GAACTTGCGGTGTGT AACC (SEQ ID NO: 40) as targeting sequences. The scramble control-siRNA plasmid was purchased from Ambion Co. The DNA fragments containing U6-Tctex-1-si and U6-control-si were inserted into pCAGIG vector in which the GFP-cDNA is under the control of chick actin-minimal CMV (CAG) promoter; the resulting plasmids were referred to as Tctex-1-si/GFP and control-si/GFP, respectively. Flag-DIC expression vector was constructed by inserting PCR fragment (5'-GTTGAGCTGTAAC-CGGGGTCTG (SEQ ID NO: 45); 5'-CGGGATCCGCAT-GTCAGACAAAAGTGAATTAAAAG (SEQ ID NO: 41)) of rat DIC2 into pRK5 vector. Autosequencing was used to confirm the inserted sequences. Expression vectors encoding GFP pEGFP-C1 (BD Biosciences, Palo Alto, Calif.), FLAG-Tctex-1 (Chuang, J. Z., et al. (2001). J Neurosci 21, 5501-5512), myc-p50 dynamintin, YFP-GalT, GFP-DIC, DHC-siRNA, myc-Rac1 L61, HA-Rho G14V and HA-Rac1T17N were used. mAbs recognizing Flag (clone M2), tyr-tubulin (clone TUB1A2), MAP2 (clone AP20), and DHC and rabbit anti-Flag Ab were from Sigma (St. Louis, Mo.). mAbs for myc (clone 9E10) and HA (clone 12CA5) were from Santa Cruz Biotechnology (Santa Cruz, Calif.). mAbs for DIC, and TuJ1 were from Chemicon (Temecula, Calif.), Tau1 mAb was from Roche (Indianapolis, Ind.), p150glued mAb was from BD Biosciences, Rat mAb YL1/2 against tyr-tubuline was from Dr. G. Gunderson (Columbia University) and Rabbit anti-GFP Ab and Alexa dye-conjugated secondary Abs were purchased from Molecular Probe (Eugene, Oreg.). Affinity-purified anti-Tctex-1 rabbit IgG was described in Tai, A. W., et al. (1998) *J Biol Chem* 273, 19639-19649.

Adenoviruses encoding Tctex-1 and GFP were produced using the AdEasy system (Stratagene, La Jolla, Calif.). The shuttle vector was prepared by placing Tctex-1 into pTrack Shuttle vector. Adenovirus was amplified and purified as described in Tai, A. W., et al. (2001). *J Cell Biol* 153, 1499-1509. Adenovirus encoding GFP was from Dr. F. Packe-Peterson (Weill Medical College, Cornell).

Culture, Transfection, and Immunochemical Analyses of Hippocampal Neurons

Embryonic hippocampal neuron cultures were prepared as described in Goslin, K., and Banker, G. (1991). Rat hippocampal neurons in low density culture. (Cambridge, Mass., MIT). AS oligos (5 μM) were added twice into culture medium, at 2 h and 12 h after plating. For transfection, either plasmid (1-4 μg) or siRNA oligonucleotide (133 nM) were mixed with Lipofectamine 2000 and added into either freshly trypsin-dissociated hippocampal neurons, neurons 2 h after plating, or neurons cultured 3 DIV. Neurons were fixed at the indicated time and processed for immunolabeling as described (Paglini, G., et al. (1998) *J Cell Biol* 143, 443-455). FITC- or TRITC-phalloidin were added during the secondary antibody incubation. All immunostained cells were analyzed by Leica TCS SP2 spectral confocal system (Nussloch, Germany) or Zeiss confocal microscope. At least 3 independent experiments were conducted for each manipulation, with 15-40 coverslips and 50-100 cells examined in each experiment. Quantification of labeling intensities and morphometric analyses were carried out by using Metamorph software (Universal Imaging Co., Downingtown, Pa.) as described (Kunda, P., et al. (2001) *J Neurosci* 21, 2361-2372. In some experiments, transfected neurons were cultured and prepared according to the procedures described by Paglini et al., (1998) for time-lapse imaging analysis.

Rac1 Activity Assays

Protein extracts of siRNA-transfected neurons or adenovirus-infected NIH 3T3 cells were subjected to Rac1 activity assays following the manufacturer's instructions (Cytoskeleton, Denver, Colo.). Briefly, the GTP-bound form of Rac1 was affinity purified by GST agarose containing the Rac binding domain of Pak1. GTP-bound Rac1 or total cell lysates were immunoblotted with anti-Rac1 antibody (BD Transduction Lab, San Diego, Calif.) using the ECL method.

Other Methods

Site-directed mutagenesis of Flag-Tctex-1 was carried out using Quickchange (Stratagene, La Jolla, Calif.). Velocity density gradient sedimentation, immunoprecipitation and immunoblotting assays were carried out essentially as described in Tai et al., (1998).

The practice of the present invention may also employ in part, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLE 6

Tctex-1 Promotes Neurogenesis

Tctex-1 polypeptides may promote proliferation of neuronal progenitors (neurogenesis) by helping to maintain neuronal peogenitors in an anti-differenation and/or proliferative state (i.e., out of the G0 cell-cycle phase).

Embryonic stem (ES) cells, their progeny, or other cells capable of assuming a neuronal fate, may be induced to express Tctex-1 polypeptides in order to promote their proliferation. This induction may be accomplished in a variety of ways. For example, the ES or neuronal progenitor cells may be transfected with a transgene that drives Tctex-1 expression under the control of a constitutive promoter, a neuronal-specific constitutive promoter, and/or an inducible promoter. For example, ES or neuronal progenitor cells may be transfected with a transgene encoding Tctex-1 under control of a tetracycline-responsive element (generated, for example, by cloning a Tctex-1 cDNA into the multiple clonging site of the pTre vector) and also with a transgene encoding a tetracycline transcriptional activator (such as pTet-On, Clontech catalogue number 631018). Such cotransfected ES or other neuronal progenitor cells may be introduced into a subject in need of neuronal repair or neuronal regenerator and then induced to express Tctex-1 by administering tetracycline or derivatives (such as doxycycline) to the subject. The cells may be introduced at a ventricular zone, at a site of injury, or at another location in the subject.

Equivalents

The present invention provides in part novel Tctex-1 and Rp3 polypeptides that stimulate neurite outgrowth. While specific embodiments of the subject invention have been discussed, the above specification is illustrative and not restrictive. Many variations of the invention will become apparent to those skilled in the art upon review of this specification. The appendant claims are not intended to claim all such embodiments and variations, and the full scope of the invention should be determined by reference to the claims, along with their full scope of equivalents, and the specification, along with such variations.

All publications and patents mentioned herein, including those items listed below, are hereby incorporated by reference in their entireties as if each individual publication or patent was specifically and individually indicated to be incorporated by reference. In case of conflict, the present application, including any definitions herein, will control.

---

The invention claimed is:

1. A recombinant polypeptide comprising an amino acid sequence having at least about 95% identity to the amino acid sequence of SEQ ID NO: 42, wherein the amino acid residue at position 94 in SEQ ID NO: 42 is glutamate, and wherein the polypeptide stimulates neurite outgrowth in vitro.

2. The polypeptide of claim 1, wherein the amino acid residue at position 82 in SEQ ID NO: 42 is serine.

3. The polypeptide of claim 1, wherein the neurite-outgrowth-stimulating polypeptide is fused to a second polypeptide.

4. The polypeptide of claim 3, wherein the second polypeptide comprises an 11 arginine protein transduction domain.

5. The polypeptide of claim 1, wherein the neurite-outgrowth-stimulating polypeptide comprises an amino acid sequence having at least about 96% identity to the amino acid sequence of SEQ ID NO: 42.

6. The polypeptide of claim 1, wherein the neurite-outgrowth-stimulating polypeptide comprises an amino acid sequence having at least about 97% identity to the amino acid sequence of SEQ ID NO: 42.

7. The polypeptide of claim 1, wherein the neurite-outgrowth-stimulating polypeptide comprises an amino acid sequence having at least about 98% identity to the amino acid sequence of SEQ ID NO: 42.

8. The polypeptide of claim 1, wherein the neurite-outgrowth-stimulating polypeptide comprises an amino acid sequence having at least about 99% identity to the amino acid sequence of SEQ ID NO: 42.

9. The polypeptide of claim 1, wherein the neurite-outgrowth-stimulating polypeptide comprises the amino acid sequence of SEQ ID NO: 42.

10. The polypeptide of claim 9, wherein the amino acid residue at position 82 in SEQ ID NO: 42 is serine.

11. The polypeptide of claim 1, wherein the polypeptide is an isolated polypeptide.

12. The polypeptide of claim 1, wherein the polypeptide is a purified polypeptide.

* * * * *

SEQUENCE LISTING

```
<160> NUMBER OF SEQ ID NOS: 45

<210> SEQ ID NO 1
<211> LENGTH: 113
<212> TYPE: PRT
<213> ORGANISM: Bos taurus

<400> SEQUENCE: 1

Met Glu Asp Tyr Gln Ala Ala Glu Glu Thr Ala Phe Val Val Asp Glu
 1               5                  10                  15

Val Ser Asn Ile Val Lys Glu Ala Ile Glu Ser Ala Ile Gly Gly Asn
                20                  25                  30

Ala Tyr Gln His Ser Lys Val Asn Gln Trp Thr Thr Asn Val Val Glu
            35                  40                  45

Gln Thr Leu Ser Gln Leu Thr Lys Leu Gly Lys Pro Phe Lys Tyr Ile
        50                  55                  60

Val Thr Cys Val Ile Met Gln Lys Asn Gly Ala Gly Leu His Thr Ala
    65                  70                  75                  80

Ser Ser Cys Phe Trp Asp Ser Ser Thr Asp Gly Ser Cys Thr Val Arg
                    85                  90                  95

Trp Glu Asn Lys Thr Met Tyr Cys Ile Val Ser Ala Phe Gly Leu Ser
                100                 105                 110

Ile
```

<210> SEQ ID NO 2
<211> LENGTH: 759
<212> TYPE: DNA
<213> ORGANISM: Bos taurus

<400> SEQUENCE: 2

| | | | | | |
|---|---|---|---|---|---|
| ggcacgagcg | gcgacgcgcg | ggcggcaaga | tggaagacta | ccaggccgcc | gaggagactg | 60 |
| cttttgttgt | tgatgaagtg | agcaacatcg | taaaagaggc | catagaaagc | gccatcggtg | 120 |
| gcaacgccta | tcagcacagc | aaagtcaatc | agtggaccac | aaacgtagtg | agcagacct | 180 |
| taagccaact | caccaagctg | gggaagccat | ttaagtacat | cgtgacctgt | gtgatcatgc | 240 |
| agaagaatgg | agcgggcctg | cacacggcaa | gctcgtgctt | ctgggacagc | tccaccgatg | 300 |
| ggagctgcac | cgtgcgatgg | gagaacaaga | ccatgtactg | catcgtcagc | gccttcggcc | 360 |
| tgtccatctg | acagccgccc | cgcccgacct | ctctccttcc | accacatccc | ttctctccca | 420 |
| tcttctaaca | ccgaccggct | atacagcgat | ctccttctc | atccaaagtg | tgtttttgtg | 480 |
| gcactctcaa | catgtagaga | aaaaaacaaa | taaccacact | gctcctctgt | gacctgcaca | 540 |
| ccaagtcaga | ggcgtcgtca | ccgcaggtag | caggagcctg | tcctgccgct | tgtcttaact | 600 |
| ctgaatgttt | cttctcaaag | gtgctaaaag | ccgaaatctg | ctagtgtgaa | actttctcta | 660 |
| ctctctgaaa | cgaatcaaat | acactaattt | tccatacttt | gtacttttg | ttagaataat | 720 |
| aaattattaa | gatttaaaaa | aaaaaaaaaa | aaaaaaaa | | | 759 |

<210> SEQ ID NO 3
<211> LENGTH: 113
<212> TYPE: PRT
<213> ORGANISM: Homo sapiens

<400> SEQUENCE: 3

Met Glu Asp Tyr Gln Ala Ala Glu Glu Thr Ala Phe Val Val Asp Glu
  1               5                  10                  15

Val Ser Asn Ile Val Lys Glu Ala Ile Glu Ser Ala Ile Gly Gly Asn
             20                  25                  30

Ala Tyr Gln His Ser Lys Val Asn Gln Trp Thr Thr Asn Val Val Glu
         35                  40                  45

Gln Thr Leu Ser Gln Leu Thr Lys Leu Gly Lys Pro Phe Lys Tyr Ile
     50                  55                  60

Val Thr Cys Val Ile Met Gln Lys Asn Gly Ala Gly Leu His Thr Ala
 65                  70                  75                  80

Ser Ser Cys Phe Trp Asp Ser Ser Thr Asp Gly Ser Cys Thr Val Arg
                 85                  90                  95

Trp Glu Asn Lys Thr Met Tyr Cys Ile Val Ser Ala Phe Gly Leu Ser
            100                 105                 110

Ile

<210> SEQ ID NO 4
<211> LENGTH: 342
<212> TYPE: DNA
<213> ORGANISM: Homo sapiens

<400> SEQUENCE: 4

| | | | | | |
|---|---|---|---|---|---|
| atggaagact | accaggctgc | ggaggagact | gcttttgttg | ttgatgaagt | gagcaacatt | 60 |
| gtaaaagagg | ctatagaaag | cgcaattggt | ggtaacgctt | atcaacacag | caaagtgaac | 120 |
| cagtggacca | caaatgtagt | agaacaaact | ttaagccaac | tcaccaagct | gggaaaacca | 180 |

```
tttaaataca tcgtgacctg tgtaattatg cagaagaatg agctggatt acacacagca    240 agttcctgct tctgggacag ctctactgac gggagctgca ctgtgcgatg ggagaataag    300
accatgtact gcatcgtcag tgccttcgga ctgtctattt aa                      342
```

<210> SEQ ID NO 5
<211> LENGTH: 113
<212> TYPE: PRT
<213> ORGANISM: Rattus norvegicus

<400> SEQUENCE: 5

```
Met Glu Asp Phe Gln Ala Ser Glu Glu Thr Ala Phe Val Val Asp Glu
 1               5                  10                  15

Val Ser Asn Ile Val Lys Glu Ala Ile Glu Ser Ala Ile Gly Gly Asn
            20                  25                  30

Ala Tyr Gln His Ser Lys Val Asn Gln Trp Thr Thr Asn Val Val Glu
        35                  40                  45

Gln Thr Leu Ser Gln Leu Thr Lys Leu Gly Lys Pro Phe Lys Tyr Ile
    50                  55                  60

Val Thr Cys Val Ile Met Gln Lys Asn Gly Ala Gly Leu His Thr Ala
65                  70                  75                  80

Ser Ser Cys Phe Trp Asp Ser Ser Thr Asp Gly Ser Cys Thr Val Arg
                85                  90                  95

Trp Glu Asn Lys Thr Met Tyr Cys Ile Val Ser Ala Phe Gly Leu Ser
            100                 105                 110

Ile
```

<210> SEQ ID NO 6
<211> LENGTH: 698
<212> TYPE: DNA
<213> ORGANISM: Rattus norvegicus

<400> SEQUENCE: 6

```
gcgctagagg gaagatggaa gacttccagg cctccgagga gactgcattt gttgtggatg     60
aagtgagcaa cattgtaaag gaggctatag aaagtgccat cggcggtaac gcctaccagc    120
acagcaaagt caaccagtgg accactaatg ttgtagaaca gactttgagc caactcacca    180
aactggggaa accatttaaa tacattgtga cctgtgtgat catgcagaag aatggtgctg    240
ggttacacac cgcaagttcc tgcttctggg acagctccac ggacgggagc tgcacagtcc    300
gatgggagaa caagaccatg tactgcatcg tcagtgcctt cggactgtcc atctgaccgc    360
ctgactgcct cagcctccgg ttccagcgtt tctagtccat cttaccacca gctatgttgg    420
gcggatacct tcctcctctt taagttgttc tgaggcactc ccaaaatgta gagaaataaa    480
ccaaatgacc ctggccacag gaaccacacg acggacacta ggcagatgag cagccacctg    540
tcatccaagg caggcagtac cagttgtctt aactgtcttc tcaaaggtgc taagatctca    600
agtctgctag tggaaacttc tctactttct gaaatgattc agatacacta attttccaca    660
ctttatactt ttgttagaat aataaattat tcagaatt                            698
```

<210> SEQ ID NO 7
<211> LENGTH: 113
<212> TYPE: PRT
<213> ORGANISM: Mus musculus

<400> SEQUENCE: 7

```
Met Glu Asp Phe Gln Ala Ser Glu Glu Thr Ala Phe Val Val Asp Glu
 1               5                  10                  15
```

Val Ser Ser Ile Val Lys Glu Ala Ile Glu Ser Ala Ile Gly Gly Asn
             20                  25                  30

Ala Tyr Gln His Ser Lys Val Asn Gln Trp Thr Thr Asn Val Leu Glu
         35                  40                  45

Gln Thr Leu Ser Gln Leu Thr Lys Leu Gly Arg Pro Phe Lys Tyr Ile
     50                  55                  60

Val Thr Cys Val Ile Met Gln Lys Asn Gly Ala Gly Leu His Ser Ala
 65                  70                  75                  80

Ser Ser Cys Phe Trp Asp Ser Ser Thr Asp Gly Ser Cys Thr Val Arg
                 85                  90                  95

Trp Glu Asn Lys Thr Met Tyr Cys Ile Val Ser Thr Phe Gly Leu Ser
                100                 105                 110

Ile

<210> SEQ ID NO 8
<211> LENGTH: 791
<212> TYPE: DNA
<213> ORGANISM: Mus musculus

<400> SEQUENCE: 8
tggtagtggt cagggtcccc cgcgcggggg cggagtgggc gtggcctgac cgcgcctgcg     60
cagtccactc tactcggcgg gcgaaggaga tgcgttaaag atggaagact ccaggcctc    120
agaggagact gcatttgttg ttgatgaagt gagcagcatt gtaaaggagg ctatagaaag    180
cgccatcggt ggtaatgcct accagcacag caaagtcaac cagtggacca ctaatgtcct    240
agaacagact ttgagccaac tcaccaaact ggggagacca tttaaataca ttgtgacctg    300
tgtgatcatg cagaagaacg gtgctgggtt acactccgca agttcctgct ctgggacag    360
ctccacagac ggaagctgca cagtccgatg ggagaacaag accatgtact gcatcgtcag    420
taccttcgga ctgtccatct gaccaccttg ccagcctcag cctcgtggtc ccagcatttc    480
cagtccatct taaccaccag ctatgttggg caaacccctt cctcctaagt tgttctgtgg    540
cactctcaaa aaaccaaatg actccccagt cacaggaacc acatgacttc agccagatta    600
gcagccacct gtcatctgag ccaggcagta ccacttgtct taactgtctt ctccaaggtg    660
ctaaaaactc aagtctgctg gtggaaacag ctctactttc tgaaatgatt cagatacact    720
aactttccat actttattct ttcttagaat aataaattat tcaaaattaa aaaaaaaaa    780
aaaaaaaaa a                                                         791

<210> SEQ ID NO 9
<211> LENGTH: 113
<212> TYPE: PRT
<213> ORGANISM: Xenopus tropicalis

<400> SEQUENCE: 9

Met Asp Glu Phe Gln Thr Ala Glu Glu Ser Ser Phe Val Val Asp Glu
  1               5                  10                  15

Ile Ser Asn Ile Ile Lys Glu Ser Ile Glu Ser Ala Ile Gly Gly Asn
             20                  25                  30

Ala Tyr Gln His Asn Lys Val Asn Gln Trp Thr Thr Asn Val Val Glu
         35                  40                  45

Gln Thr Leu Ser Gln Leu Thr Lys Leu Gly Lys Pro Phe Lys Tyr Ile
     50                  55                  60

Val Thr Cys Val Ile Met Gln Lys Asn Gly Ala Gly Leu His Thr Ala
 65                  70                  75                  80

Ser Ser Cys Phe Trp Asp Asn Ala Thr Asp Gly Ser Cys Thr Val Arg
            85                  90                  95

Trp Glu Asn Lys Thr Met Tyr Cys Ile Val Ser Ala Phe Gly Leu Ala
        100                 105                 110

Ile

<210> SEQ ID NO 10
<211> LENGTH: 1095
<212> TYPE: DNA
<213> ORGANISM: Xenopus tropicalis

<400> SEQUENCE: 10
tgcagggtgg ctgctggtgc ggacgttgtt ggtagtggga aagatggatg aatttcaaac      60
ggcagaggag tcttcatttg tagtggatga aataagcaac atcattaaag agtcaattga     120
aagtgccatc ggtggtaatg cttaccagca caacaaagtg aaccagtgga ctactaatgt     180
ggtagaacag acactcagtc agcttacaaa gttgggcaag ccgttcaaat acatagtgac     240
ctgtgtaatt atgcaaaaga atggtgcagg acttcataca gcaagctctt gcttctggga     300
taatgcaacg gatggaagct gtaccgtgag atgggagaac aagactatgt actgtattgt     360
cagtgccttt ggacttgcaa ataatttttt caattcctga ttgttttttt ataaattcat     420
actctgacaa cacctttttg agttaaagaa aattcttatt ttttcatctg aaagaatgct     480
atttttttg gctattcagc attataacca ttagtactaa accaaatcta aaatcttctg     540
cattatctta tttaaggtgc tacaagctac tatcaagtgc cacaacaaat tgcctgatct     600
tgttcatcaa atacaataat tgttacattt gttaccttag ctaatactaa attattgaat     660
acatgcttta tattttaca gtgtaatttc cactgtgtca ttggttctac ctggcatcca     720
ccattttcct tcctgttttt tgtcactgtg taaaaacaaa caattaata tggcagatat     780
attttttagg actagtctgt catttgtgtc tcaacttgtt aatttttttt gcatcacttt     840
tcatgtgtgc actgtcttaa tatcacaatt tcactaataa cttgtgttaa cagcatggat     900
gggttttttt tagaatgacc taatgcaaag acttgtattt atgttgttaa aaaaataaat     960
gcatggcaag aaaagcatca aaggtttcag gctatttag gcagtttcac tgtgcattgg    1020
gaggtgtgtt gtacccaagg agaaaataaa ttttgccaga cttgaaaaaa aaaaaaaaa    1080
aaaaaaaaaa aaaaa                                                   1095

<210> SEQ ID NO 11
<211> LENGTH: 111
<212> TYPE: PRT
<213> ORGANISM: Drosophila melanogaster

<400> SEQUENCE: 11

Met Asp Asp Ser Arg Glu Glu Ser Gln Phe Ile Val Asp Asp Val Ser
 1               5                  10                  15

Lys Thr Ile Lys Glu Ala Ile Glu Thr Thr Ile Gly Gly Asn Ala Tyr
            20                  25                  30

Gln His Asp Lys Val Asn Asn Trp Thr Gly Gln Val Val Glu Asn Cys
        35                  40                  45

Leu Thr Val Leu Thr Lys Glu Gln Lys Pro Tyr Lys Tyr Ile Val Thr
    50                  55                  60

Ala Met Ile Met Gln Lys Asn Gly Ala Gly Leu His Thr Ala Ser Ser
65                  70                  75                  80

Cys Tyr Trp Asn Asn Asp Thr Asp Gly Ser Cys Thr Val Arg Trp Glu

|   | 85 | 90 | 95 |
|---|---|---|---|

Asn Lys Thr Met Tyr Cys Ile Val Ser Val Phe Gly Leu Ala Val
                100                 105                 110

<210> SEQ ID NO 12
<211> LENGTH: 551
<212> TYPE: DNA
<213> ORGANISM: Drosophila melanogaster

<400> SEQUENCE: 12

```
cttagaaaaa tagaatcccg atatatatta tttggactgc tcgaacgccg ccgacgagcc      60
caaaaacgcg cgcacattta caacgacaac aatacaaact tgagctcagt acgtaaactt     120
ttttgaccag ctgccgttag aagcaaatca aagctgcgac gatggatgac tcacgcgaag     180
aaagccagtt cattgtggac gacgtgagca agacgattaa agaggccatc gagacgacca     240
tcggcggtaa cgcctaccag cacgacaagg tgaacaactg gaccggccag gtggtggaga     300
actgcctgac ggtgctcacc aaggagcaga agccctacaa gtacattgtg accgccatga     360
tcatgcaaaa gaacggtgct ggactccaca ccgccagctc ctgctactgg aacaacgaca     420
ccgacggatc gtgcacagta cgctgggaga acaagaccat gtactgcatc gtttcggtct     480
tcggactggc cgtctagagt ggaggaatgg caggactgcc ggaattcgca tgaaaatgac     540
ttagaagggg g                                                         551
```

<210> SEQ ID NO 13
<211> LENGTH: 115
<212> TYPE: PRT
<213> ORGANISM: Danio rerio

<400> SEQUENCE: 13

Met Glu Glu Tyr His Ser Gly Asp Glu Val Ser Phe Asn Pro Asp Asp
  1               5                  10                  15

Ala Ser Asn Val Val Lys Glu Cys Ile Glu Gly Ile Gly Gly Val
                 20                  25                  30

Asp Tyr Ser Gln Asn Lys Val Asn Gln Trp Thr Ala Ser Ile Val Glu
             35                  40                  45

His Ser Leu Thr Gln Leu Val Lys Gln Gly Lys Pro Phe Lys Tyr Ile
         50                  55                  60

Val Asn Cys Ala Val Met Gln Lys Ser Gly Ala Gly Leu His Thr Ala
 65                  70                  75                  80

Asn Ser Cys Tyr Trp Asp Thr Thr Asp Gly Ser Cys Thr Val Arg
                 85                  90                  95

Trp Glu Asn Arg Thr Met Tyr Cys Val Val Ser Val Phe Ala Val Ala
                100                 105                 110

Ile Ala Leu
        115

<210> SEQ ID NO 14
<211> LENGTH: 1170
<212> TYPE: DNA
<213> ORGANISM: Danio rerio

<400> SEQUENCE: 14

```
acatcagtct gttgtcagtg aaagaaaaga tacagtcgtc tgagtttgcc gtccagattt      60
ttggtgtttt ttaagctgaa aagatggagg agtatcattc tggagatgaa gtttctttca     120
acccagatga tgcaagtaat gttgtaaagg agtgcatcga ggggattatt ggtggtgtgg     180
```

```
actacagcca gaacaaagtc aaccagtgga cggccagcat agtcgagcac tctctcactc    240
agttagtcaa acaaggcaaa cccttcaaat acattgtcaa ctgtgctgtg atgcagaaaa    300
gcggcgcagg tcttcacaca gccaactctt gttattggga cactaccact gacggaagtt    360
gcacagtgag gtgggagaac cggactatgt attgcgtcgt cagtgtgttt gcagtggcca    420
ttgcactatg agctgagtcc cacacatgca cacacacaca cacacacaca cacacacact    480
gaagatcaaa gccagcttca ctcacatgtc tattattaag cttttttgctt caacacatcg    540 gcttaaacat cacccatgtt tagctcctgt ctgtttggcc tgatacaatg tttagactga    600
attgtaagct cttatctact acaatgtatc tatatttgct tctctgtttt tggacctgca    660
aaggtatcat gcacctttgc tctgtataga atgaaatgaa aatttgttga tggtaattat    720
taaagtagtt tgtttgggt ttaataatac agtgttatga attcatctga atggttttt     780 ttttagtttt cagccaccaa agggcatgca actttgttta agcttgacat aaagacagag    840 aaaatgtaaaa ttattcacac atgatgtacg aatgtcatgt catgtcataa tagttgttca   900
gcattatttt agggaattga aaatgagttt tatccccggc tcttaagttt aaaaacagcc    960
agaacacaat cattttgctg aaagatttat acaagaaaat gacttttttgt ttgtttgttt   1020 gtttgtttat ttattcagtt aattaaccac acacacattt cctctacaat aatgttaaat   1080
aattgaattg ccaaatctta ttaacatgaa aaacaagtac tggaattaaa agctttgttt   1140
gattcactaa aaaaaaaaaa aaaaaaaaa                                     1170
```

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Glu Asp Tyr Gln Ala Ala Glu Glu Thr Ala Phe Val Val Asp Glu
 1               5                  10                  15

Val Ser Asn Ile Val Lys Glu Ala Ile Glu Ser Ala Ile Gly Gly Asn
            20                  25                  30

Ala Tyr Gln His Ser Lys Val Asn Gln Trp Thr Thr Asn Val Val Glu
        35                  40                  45

Gln Thr Leu Ser Gln Leu Thr Lys Leu Gly Lys Pro Phe Lys Tyr Ile
    50                  55                  60

Val Thr Cys Val Ile Met Gln Lys Asn Gly Ala Gly Leu His Thr Ala
65                  70                  75                  80

Ser Ser Cys Phe Trp Asp Ser Ser Thr Asp Gly Ser Cys Glu Val Arg
                85                  90                  95

Trp Glu Asn Lys Thr Met Tyr Cys Ile Val Ser Ala Phe Gly Leu Ser
            100                 105                 110

Ile
```

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

-continued

Met Glu Asp Tyr Gln Ala Ala Glu Glu Thr Ala Phe Val Val Asp Glu
1               5                   10                  15

Val Ser Asn Ile Val Lys Glu Ala Ile Glu Ser Ala Ile Gly Gly Asn
            20                  25                  30

Ala Tyr Gln His Ser Lys Val Asn Gln Trp Thr Thr Asn Val Val Glu
        35                  40                  45

Gln Thr Leu Ser Gln Leu Thr Lys Leu Gly Lys Pro Phe Lys Tyr Ile
    50                  55                  60

Val Thr Cys Val Ile Met Gln Lys Asn Gly Ala Gly Leu His Thr Ala
65                  70                  75                  80

Ser Glu Cys Phe Trp Asp Ser Ser Thr Asp Gly Ser Cys Thr Val Arg
                85                  90                  95

Trp Glu Asn Lys Thr Met Tyr Cys Ile Val Ser Ala Phe Gly Leu Ser
            100                 105                 110

Ile

<210> SEQ ID NO 17
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Glu Asp Tyr Gln Ala Ala Glu Glu Thr Ala Phe Val Val Asp Glu
1               5                   10                  15

Val Ser Asn Ile Val Lys Glu Ala Ile Glu Ser Ala Ile Gly Gly Asn
            20                  25                  30

Ala Tyr Gln His Ser Lys Val Asn Gln Trp Thr Thr Asn Val Val Glu
        35                  40                  45

Gln Thr Leu Ser Gln Leu Thr Lys Leu Gly Lys Pro Phe Lys Tyr Ile
    50                  55                  60

Val Thr Cys Val Ile Met Gln Lys Asn Gly Ala Gly Leu His Thr Ala
65                  70                  75                  80

Ser Ala Cys Phe Trp Asp Ser Ser Thr Asp Gly Ser Cys Thr Val Arg
                85                  90                  95

Trp Glu Asn Lys Thr Met Tyr Cys Ile Val Ser Ala Phe Gly Leu Ser
            100                 105                 110

Ile

<210> SEQ ID NO 18
<211> LENGTH: 116
<212> TYPE: PRT
<213> ORGANISM: Homo sapiens

<400> SEQUENCE: 18

Met Glu Glu Tyr His Arg His Cys Asp Glu Val Gly Phe Asn Ala Glu
1               5                   10                  15

Glu Ala His Asn Ile Val Lys Gly Cys Val Asp Gly Val Leu Gly Gly
            20                  25                  30

Glu Asp Tyr Asn His Asn Asn Ile Asn Gln Trp Thr Ala Ser Ile Val
        35                  40                  45

Glu Gln Ser Leu Thr His Leu Val Lys Leu Gly Lys Ala Tyr Lys Tyr
    50                  55                  60

Ile Val Thr Cys Ala Val Val Gln Lys Ser Ala Tyr Gly Phe His Thr
65                  70                  75                  80

```
Ala Ser Ser Cys Phe Trp Asp Thr Thr Ser Asp Gly Thr Cys Thr Val
                85                  90                  95
Arg Trp Glu Asn Arg Thr Met Asn Cys Ile Val Asn Val Phe Ala Ile
            100                 105                 110
Ala Ile Val Leu
        115

<210> SEQ ID NO 19
<211> LENGTH: 351
<212> TYPE: DNA
<213> ORGANISM: Homo sapiens

<400> SEQUENCE: 19
atggaggagt accatcgcca ctgcgacgag gttggcttca atgctgagga agcccacaat      60
attgtcaaag agtgtgtaga tggggtttta ggtggtgaag attataatca caacaacatc     120
aaccagtgga ctgcaagcat agtggaacaa tccttaacac acctggttaa gttgggaaaa     180
gcctataaat atattgtgac ctgtgcagtg gtccagaaga gcgcatatgg ctttcacaca     240
gccagctcct gttttggga taccacatct gatggaacct gtaccgtaag atgggagaac      300
cggaccatga actgtattgt caacgttttt gccattgcta ttgttcttta a              351

<210> SEQ ID NO 20
<211> LENGTH: 116
<212> TYPE: PRT
<213> ORGANISM: Pongo pygmaeus

<400> SEQUENCE: 20

Met Glu Glu Tyr His Arg His Cys Asp Glu Val Gly Phe Asn Ala Glu
  1               5                  10                  15
Glu Ala His Asn Ile Val Lys Glu Cys Val Asp Gly Val Leu Gly Gly
             20                  25                  30
Glu Asp Tyr Asn His Asn Asn Ile Asn Gln Trp Thr Ala Ser Ile Val
         35                  40                  45
Glu Gln Ser Leu Thr His Leu Val Lys Leu Gly Lys Ala Tyr Lys Tyr
     50                  55                  60
Ile Val Thr Cys Ala Val Val Gln Lys Ser Ala Tyr Gly Phe His Thr
 65                  70                  75                  80
Ala Ser Ser Cys Phe Trp Asp Thr Thr Ser Asp Gly Thr Cys Thr Val
                85                  90                  95
Arg Trp Glu Asn Arg Thr Met Asn Cys Ile Val Asn Val Phe Ala Ile
            100                 105                 110
Ala Ile Val Leu
        115

<210> SEQ ID NO 21
<211> LENGTH: 351
<212> TYPE: DNA
<213> ORGANISM: Pongo pygmaeus

<400> SEQUENCE: 21
atggaggagt accatcgcca ctgcgacgag gttggcttca atgctgagga agcccacaat      60
attgtcaaag agtgtgtaga tggggtttta ggtggtgaag attataatca caacaacatc     120
aaccagtgga ccgcaagcat agtggaacaa tccttaacac atctggttaa gttgggaaaa     180
gcttataaat atattgtgac ctgtgcagtg gtccagaaga gcgcatatgg ctttcacaca     240
gccagctcct gttttggga taccacatct gatggaacct gtaccgtaag atgggagaac      300
```
cggaccatga actgtattgt caatgttttt gccattgcta ttgttctttta a         351

<210> SEQ ID NO 22
<211> LENGTH: 116
<212> TYPE: PRT
<213> ORGANISM: Canis familiaris

<400> SEQUENCE: 22

Met Glu Glu Tyr His Arg His Cys Asp Glu Val Gly Phe Asn Ala Asp
1               5                   10                  15

Glu Ala His Asn Ile Val Lys Glu Cys Ile Asp Gly Val Leu Gly Gly
            20                  25                  30

Glu Asp Tyr Asn Gln Asn Asn Ile Asn Gln Trp Thr Ala Ser Ile Val
        35                  40                  45

Glu Gln Ser Leu Thr His Leu Val Lys Leu Gly Lys Ala Tyr Lys Tyr
    50                  55                  60

Ile Val Thr Cys Ala Val Val Gln Arg Ser Ala Tyr Gly Phe His Thr
65                  70                  75                  80

Ala Ser Ser Cys Phe Trp Asp Thr Thr Ser Asp Gly Thr Cys Thr Val
                85                  90                  95

Arg Trp Glu Asn Arg Thr Met Asn Cys Ile Val Asn Val Phe Ala Ile
            100                 105                 110

Ala Ile Val Leu
        115

<210> SEQ ID NO 23
<211> LENGTH: 351
<212> TYPE: DNA
<213> ORGANISM: Canis familiaris

<400> SEQUENCE: 23
atggaggagt accacaggca ctgcgacgag gttggcttca atgctgatga agctcacaat     60
attgtgaagg agtgtataga tggggtcttg ggtggtgaag attataacca gaacaacatc    120
aaccaatgga ctgcaagcat agtggaacaa tccttaacac atttggttaa gttgggaaaa    180
gcttataaat atattgtgac ctgtgcagtg gtccagagga gtgcctatgg ctttcacaca    240
gccagctcat gttttggga caccacatct gatggaacct gtaccgtaag atgggagaac    300
cgaaccatga actgtattgt caatgttttt gccattgcta ttgttctgtg a             351

<210> SEQ ID NO 24
<211> LENGTH: 116
<212> TYPE: PRT
<213> ORGANISM: Ovis aries

<400> SEQUENCE: 24

Met Glu Glu Tyr His Arg Pro Cys Asp Glu Val Gly Phe Asn Ala Asp
1               5                   10                  15

Glu Ala His Asn Ile Val Lys Glu Cys Ile Asp Gly Val Leu Gly Gly
            20                  25                  30

Glu Asp Tyr Asn Gln Asn Asn Ile Asn Gln Trp Thr Ala Ser Ile Val
        35                  40                  45

Glu Gln Ser Leu Ala His Leu Val Lys Leu Gly Lys Ala Tyr Lys Tyr
    50                  55                  60

Ile Val Thr Cys Ala Val Val Gln Arg Ser Pro Tyr Gly Phe His Thr
65                  70                  75                  80

Ala Ser Ser Cys Phe Trp Asp Thr Thr Ser Asp Gly Thr Cys Thr Val

```
                85                  90                  95
Arg Trp Glu Asn Arg Thr Met Asn Cys Ile Val Asn Val Phe Ala Ile
            100                 105                 110

Ala Ile Val Leu
        115

<210> SEQ ID NO 25
<211> LENGTH: 351
<212> TYPE: DNA
<213> ORGANISM: Ovis aries

<400> SEQUENCE: 25
atggaggagt accatcgccc ctgcgacgag gttggcttca atgctgatga agcccacaat    60
attgttaaag agtgtataga tggggtcttg ggaggtgaag attataatca gaacaatatc   120
aaccaatgga ctgcaagcat agtggaacaa tccctagcac atctggttaa gctgggaaaa   180
gcttataagt atattgtgac ctgtgccgtg gtccagagga gtccatatgg ctttcacaca   240
gccagctcat gttttttgga caccacatct gatggaacct gcactgtaag atgggagaac   300
cgaaccatga actgtatcgt caatgttttt gccattgcta ttgtcctgta g            351

<210> SEQ ID NO 26
<211> LENGTH: 116
<212> TYPE: PRT
<213> ORGANISM: Mus musculus

<400> SEQUENCE: 26

Met Glu Gly Tyr Gln Arg Pro Cys Asp Glu Val Gly Phe Asn Ala Asp
 1               5                  10                  15

Glu Ala His Asn Ile Val Lys Glu Cys Val Asp Gly Val Leu Gly Gly
            20                  25                  30

Asn Asp Tyr Asn Glu Asn Asn Ile Asn Gln Trp Thr Ala Ser Ile Val
        35                  40                  45

Glu Gln Ser Ile Thr His Leu Val Lys Leu Gly Lys Ala Tyr Lys Tyr
    50                  55                  60

Ile Val Thr Cys Ala Val Val Gln Arg Ser Pro Tyr Gly Phe His Thr
65                  70                  75                  80

Ala Ser Ser Cys Phe Trp Asp Thr Thr Ser Asp Gly Thr Cys Thr Ile
                85                  90                  95

Arg Trp Glu Asn Arg Thr Met Asn Cys Ile Val Asn Val Phe Ala Val
            100                 105                 110

Ala Ile Val Leu
        115

<210> SEQ ID NO 27
<211> LENGTH: 351
<212> TYPE: DNA
<213> ORGANISM: Mus musculus

<400> SEQUENCE: 27 atggagggt accaacggcc ctgcgatgag gttggcttca atgctgatga agcccataat     60
atagtcaaag agtgtgttga tggagttttg ggtggtaacg attataatga gaataacatc   120
aaccaatgga ctgcaagcat agtggaacag tctataacac atttggtcaa actgggaaaa   180
gcttacaagt acattgtgac ctgtgcagtg gtccagagga gcccgtatgg atttcacaca   240
gccagctcct gttttttgga tacaacatct gatggaacct gtaccatcag atgggagaac   300
cgtaccatga actgcatcgt gaatgttttt gcagttgcga ttgtcctgta g            351
```

<210> SEQ ID NO 28
<211> LENGTH: 116
<212> TYPE: PRT
<213> ORGANISM: Rattus norvegicus

<400> SEQUENCE: 28

Met Asp Gly Tyr Gln Arg Pro Cys Asp Glu Ile Gly Phe Asn Ala Glu
1               5                   10                  15

Glu Ala His Asn Ile Val Lys Glu Cys Val Glu Gly Val Leu Gly Gly
            20                  25                  30

Asn Asp Tyr Asn Gln Asn Ser Ile Asn Gln Trp Thr Ala Ser Ile Val
        35                  40                  45

Glu Gln Ser Ile Ala His Leu Val Lys Leu Gly Lys Ala Tyr Lys Tyr
    50                  55                  60

Ile Val Thr Cys Ala Val Val Gln Arg Ser Pro Tyr Gly Phe His Val
65                  70                  75                  80

Ala Ser Ser Cys Phe Trp Asp Thr Thr Ser Asp Gly Thr Cys Thr Val
                85                  90                  95

Arg Trp Glu Asn Arg Thr Met Asn Cys Val Val Asn Val Phe Ala Val
            100                 105                 110

Ala Ile Val Leu
        115

<210> SEQ ID NO 29
<211> LENGTH: 351
<212> TYPE: DNA
<213> ORGANISM: Rattus norvegicus

<400> SEQUENCE: 29
atggacgggt accagcggcc ctgcgacgag attggcttca atgctgagga agcacataat      60
atagtcaaag agtgtgttga aggagtcttg ggtggtaatg actataacca gaatagcatc     120
aaccagtgga ccgcaagcat cgttgaacaa tctatagctc atttggtcaa actggggaaa     180
gcttacaagt acatcgtgac ctgtgcagta gtccagagga gcccatatgg atttcacgtg     240
gccagctcct gttttgggga tacaacatct gatggcacct gtaccgttag atgggagaat     300
cgaaccatga actgcgttgt taatgttttt gcagtagcaa ttgtcctata a              351

<210> SEQ ID NO 30
<211> LENGTH: 115
<212> TYPE: PRT
<213> ORGANISM: Danio rerio

<400> SEQUENCE: 30

Met Glu Glu Tyr His Ser Gly Asp Glu Val Ser Phe Asn Pro Asp Asp
1               5                   10                  15

Ala Ser Asn Val Val Lys Glu Cys Ile Glu Gly Ile Ile Gly Gly Val
            20                  25                  30

Asp Tyr Ser Gln Asn Lys Val Asn Gln Trp Thr Ala Ser Ile Val Glu
        35                  40                  45

His Ser Leu Thr Gln Leu Val Lys Gln Gly Lys Pro Phe Lys Tyr Ile
    50                  55                  60

Val Asn Cys Ala Val Met Gln Lys Ser Gly Ala Gly Leu His Thr Ala
65                  70                  75                  80

Asn Ser Cys Tyr Trp Asp Thr Thr Thr Asp Gly Ser Cys Thr Val Arg
                85                  90                  95

```
Trp Glu Asn Arg Thr Met Tyr Cys Val Val Ser Val Phe Ala Val Ala
            100                 105                 110

Ile Ala Leu
        115

<210> SEQ ID NO 31
<211> LENGTH: 348
<212> TYPE: DNA
<213> ORGANISM: Danio rerio

<400> SEQUENCE: 31
atggaggagt atcattctgg agatgaagtt tctttcaacc cagatgatgc aagtaatgtt      60
gtaaaggagt gcatcgaggg gattattggt ggtgtggact acagccagaa caaagtcaac     120
cagtggacgg ccagcatagt cgagcactct ctcactcagt tagtcaaaca aggcaaaccc     180
ttcaaataca ttgtcaactg tgctgtgatg cagaaaagcg gcgcaggtct tcacacagcc     240
aactcttgtt attgggacac taccactgac ggaagttgca cagtgaggtg ggagaaccgg     300
actatgtatt gcgtcgtcag tgtgtttgca gtggccattg cactatga                  348

<210> SEQ ID NO 32
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atggaagact accaggccgc cgaggagact gcttttgttg ttgatgaagt gagcaacatc      60
gtaaaagagg ccatagaaag cgccatcggt ggcaacgcct atcagcacag caaagtcaat     120
cagtggacca caaacgtagt ggagcagacc ttaagccaac tcaccaagct ggggaagcca     180
tttaagtaca tcgtgacctg tgtgatcatg cagaagaatg gagcgggcct gcacacggca     240
agctcgtgct tctgggacag ctccaccgat gggagctgcg aagtgcgatg ggagaacaag     300
accatgtact gcatcgtcag cgccttcggc ctgtccatct ga                        342

<210> SEQ ID NO 33
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atggaagact accaggccgc cgaggagact gcttttgttg ttgatgaagt gagcaacatc      60
gtaaaagagg ccatagaaag cgccatcggt ggcaacgcct atcagcacag caaagtcaat     120
cagtggacca caaacgtagt ggagcagacc ttaagccaac tcaccaagct ggggaagcca     180
tttaagtaca tcgtgacctg tgtgatcatg cagaagaatg gagcgggcct gcacacggca     240
agcgaatgct tctgggacag ctccaccgat gggagctgca ccgtgcgatg ggagaacaag     300
accatgtact gcatcgtcag cgccttcggc ctgtccatct ga                        342

<210> SEQ ID NO 34
<211> LENGTH: 341
<212> TYPE: DNA
<213> ORGANISM: Artificial Sequence
<220> FEATURE:
<223> OTHER INFORMATION: Description of Artificial Sequence: Synthetic
```

-continued polynucleotide

<400> SEQUENCE: 34

| atggaagact | accaggccgc | cgaggagact | gcttttgttg | ttgatgaagt | gagcaacatc | 60 |
| gtaaaagagg | ccatagaaag | cgccatcggt | ggcaacgcct | atcagcacag | caaagtcaat | 120 |
| cagtggacca | caaacgtagt | ggagcagacc | ttaagccaac | tcaccaagct | ggggaagcca | 180 |
| tttaagtaca | tcgtgacctg | tgtgatcatg | cagaagaatg | gagcgggcct | gcacacggca | 240 |
| agcgcgtgct | tctgggacag | ctccaccgat | gggagctgca | ccgtgcgatg | ggagaacaag | 300 |
| accatgtact | gcatcgtcag | cgccttcggc | ctgtccatct | g | | 341 |

<210> SEQ ID NO 35
<211> LENGTH: 113
<212> TYPE: PRT
<213> ORGANISM: Bos taurus

<400> SEQUENCE: 35

Met Glu Asp Tyr Gln Ala Ala Glu Glu Thr Ala Phe Val Val Asp Glu
1               5                   10                  15

Val Ser Asn Ile Val Lys Glu Ala Ile Glu Ser Ala Ile Gly Gly Asn
            20                  25                  30

Ala Tyr Gln His Ser Lys Val Asn Gln Trp Thr Thr Asn Val Val Glu
        35                  40                  45

Gln Thr Leu Ser Gln Leu Thr Lys Leu Gly Lys Pro Phe Lys Tyr Ile
    50                  55                  60

Val Thr Cys Val Ile Met Gln Lys Asn Gly Ala Gly Leu His Thr Ala
65                  70                  75                  80

Ser Ser Cys Phe Trp Asp Ser Ser Thr Asp Gly Ser Cys Ala Val Arg
                85                  90                  95

Trp Glu Asn Lys Thr Met Tyr Cys Ile Val Ser Ala Phe Gly Leu Ser
            100                 105                 110

Ile

<210> SEQ ID NO 36
<211> LENGTH: 342
<212> TYPE: DNA
<213> ORGANISM: Bos taurus

<400> SEQUENCE: 36

| atggaagact | accaggccgc | cgaggagact | gcttttgttg | ttgatgaagt | gagcaacatc | 60 |
| gtaaaagagg | ccatagaaag | cgccatcggt | ggcaacgcct | atcagcacag | caaagtcaat | 120 |
| cagtggacca | caaacgtagt | ggagcagacc | ttaagccaac | tcaccaagct | ggggaagcca | 180 |
| tttaagtaca | tcgtgacctg | tgtgatcatg | cagaagaatg | gagcgggcct | gcacacggca | 240 |
| agctcgtgct | tctgggacag | ctccaccgat | gggagctgcg | ccgtgcgatg | ggagaacaag | 300 |
| accatgtact | gcatcgtcag | cgccttcggc | ctgtccatct | ga | | 342 |

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)
<223> OTHER INFORMATION: phospho-a

```
<220> FEATURE:
<221> NAME/KEY: modified_base
<222> LOCATION: (18)
<223> OTHER INFORMATION: phospho-a
<220> FEATURE:
<221> NAME/KEY: modified_base
<222> LOCATION: (19)
<223> OTHER INFORMATION: phospho-c

<400> SEQUENCE: 37
tgctcacttc atccacaac                                                19

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 38
gucaaccagu ggaccacuat t                                             21

<210> SEQ ID NO 39
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggttacacac cgcaagttcc ccatggggaa cttgcggtgt gtaacccttt tta          53

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agcttaaaaa gggttacaca ccgcaagttc cccatgggga acttgcggtg tgtaacc      57

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgggatccgc atgtcagaca aaagtgaatt aaaag                              35

<210> SEQ ID NO 42
<211> LENGTH: 113
<212> TYPE: PRT
<213> ORGANISM: Artificial Sequence
<220> FEATURE:
<223> OTHER INFORMATION: Description of Artificial Sequence: Synthetic
      protein
<220> FEATURE:
<221> NAME/KEY: MOD_RES
<222> LOCATION: (82)
```

```
<223> OTHER INFORMATION: variable amino acid; see specification as
      filed for detailed description of substitutions and preferred
      embodiments
<220> FEATURE:
<221> NAME/KEY: MOD_RES
<222> LOCATION: (94)
<223> OTHER INFORMATION: variable amino acid; see specification as
      filed for detailed description of substitutions and preferred
      embodiments

<400> SEQUENCE: 42

Met Glu Asp Tyr Gln Ala Ala Glu Glu Thr Ala Phe Val Val Asp Glu
 1               5                  10                  15

Val Ser Asn Ile Val Lys Glu Ala Ile Glu Ser Ala Ile Gly Gly Asn
             20                  25                  30

Ala Tyr Gln His Ser Lys Val Asn Gln Trp Thr Thr Asn Val Val Glu
         35                  40                  45

Gln Thr Leu Ser Gln Leu Thr Lys Leu Gly Lys Pro Phe Lys Tyr Ile
     50                  55                  60

Val Thr Cys Val Ile Met Gln Lys Asn Gly Ala Gly Leu His Thr Ala
 65                  70                  75                  80

Ser Xaa Cys Phe Trp Asp Ser Ser Thr Asp Gly Ser Cys Xaa Val Arg
                 85                  90                  95

Trp Glu Asn Lys Thr Met Tyr Cys Ile Val Ser Ala Phe Gly Leu Ser
                100                 105                 110

Ile

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)
<223> OTHER INFORMATION: phospho-c
<220> FEATURE:
<221> NAME/KEY: modified_base
<222> LOCATION: (17)
<223> OTHER INFORMATION: phospho-a
<220> FEATURE:
<221> NAME/KEY: modified_base
<222> LOCATION: (18)
<223> OTHER INFORMATION: phospho-a

<400> SEQUENCE: 43
tgtcacttct cacaccaa                                                18

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44
uaguggucca cugguugact t                                            21

<210> SEQ ID NO 45
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gttgagctgt aaccggggtc tg                                              22
```